US010119114B2

(12) United States Patent
Kreuwel et al.

(10) Patent No.: US 10,119,114 B2
(45) Date of Patent: *Nov. 6, 2018

(54) DEVICE FOR THE LYSIS OF MICROORGANISMS PRESENT IN AN ENVIRONMENTAL OR CLINICAL SAMPLE AND THE EXTRACTION OF NUCLEIC ACIDS FROM SAID MICROORGANISMS FOR ANALYSIS

(75) Inventors: Hermanus Johannes Maria Kreuwel, Schijndel (NL); Emiel Gerebern Maria Verwimp, Kasterlee (BE)

(73) Assignee: BIOMERIEUX, Marcy l'Etoile (FR)

( * ) Notice: Subject to any disclaimer, the term of this patent is extended or adjusted under 35 U.S.C. 154(b) by 371 days.

This patent is subject to a terminal disclaimer.

(21) Appl. No.: 12/451,486

(22) PCT Filed: Jun. 6, 2008

(86) PCT No.: PCT/FR2008/051012
§ 371 (c)(1),
(2), (4) Date: Nov. 13, 2009

(87) PCT Pub. No.: WO2009/001010
PCT Pub. Date: Dec. 31, 2008

(65) Prior Publication Data
US 2010/0075313 A1 Mar. 25, 2010

(30) Foreign Application Priority Data
Jun. 7, 2007 (FR) ..................... 07 55540

(51) Int. Cl.
*C12Q 1/68* (2018.01)
*C12M 1/00* (2006.01)
*C12M 1/12* (2006.01)

(52) U.S. Cl.
CPC ............ *C12M 47/06* (2013.01); *C12M 25/14* (2013.01); *C12Q 1/68* (2013.01)

(58) Field of Classification Search
None
See application file for complete search history.

(56) References Cited

U.S. PATENT DOCUMENTS

| | | | |
|---|---|---|---|
| 3,831,621 A | 8/1974 | Anthony et al. | |
| 4,672,040 A | 6/1987 | Josephson | |
| 5,567,050 A | 10/1996 | Zlobinsky et al. | |
| 5,707,861 A | 1/1998 | Sherman et al. | |
| 5,750,338 A | 5/1998 | Collins et al. | |
| 5,989,824 A * | 11/1999 | Birmingham et al. | 435/6.12 |
| 6,398,402 B1 | 6/2002 | Thomas et al. | |
| 6,632,662 B1 | 10/2003 | Broyer et al. | |
| 8,088,576 B2 * | 1/2012 | Gumbrecht | B01L 3/502761 435/6.1 |
| 2002/0185557 A1 | 12/2002 | Sparks | |
| 2003/0119171 A1 * | 6/2003 | Mathur | C12Q 1/24 435/243 |
| 2003/0129614 A1 * | 7/2003 | Parameswaran et al. | 435/6 |
| 2004/0038385 A1 | 2/2004 | Langlois et al. | |
| 2005/0070944 A1 | 3/2005 | Holl et al. | |
| 2005/0191620 A1 * | 9/2005 | McDevitt et al. | 435/5 |
| 2006/0073585 A1 * | 4/2006 | McDevitt | C12Q 1/04 435/288.7 |
| 2007/0015177 A1 | 1/2007 | Maron et al. | |
| 2007/0064521 A1 | 3/2007 | Miszenti | |
| 2007/0068284 A1 | 3/2007 | Castro et al. | |
| 2007/0248958 A1 * | 10/2007 | Jovanovich | B01F 11/0071 435/6.19 |
| 2009/0197299 A1 * | 8/2009 | Vargas | C12Q 1/04 435/39 |

FOREIGN PATENT DOCUMENTS

| | | |
|---|---|---|
| EP | 0 303 791 A1 | 2/1989 |
| FR | 2 607 507 A1 | 6/1988 |
| FR | 2 781 500 A1 | 1/2000 |
| FR | 2 781 802 A1 | 2/2000 |
| FR | 2 861 085 A1 | 4/2005 |
| GB | 203402 | 9/1923 |
| GB | 2 254 024 A | 9/1992 |
| WO | WO 95/08000 A2 | 3/1995 |
| WO | WO 97/45202 A1 | 12/1997 |
| WO | WO 99/35500 A1 | 7/1999 |
| WO | WO 00/73412 A2 | 12/2000 |
| WO | WO 2004/018704 A2 | 3/2004 |
| WO | WO 2004018704 A2 * | 3/2004 |
| WO | WO 2005/038025 A1 | 4/2005 |
| WO | WO 2005083391 A1 * | 9/2005 ............... C12Q 1/04 |

(Continued)

OTHER PUBLICATIONS

Boom et al., "Rapid and simple method for purification of nucleic acids," *Journal of Clinical Microbiology*, Mar. 1990, pp. 495-503, vol. 28, No. 3, American Society for Microbiology, USA.

Levison et al., "New approaches to the isolation of DNA by ion-exchange chromatography," *Journal of Chromatography A*, 1998, pp. 337-344, vol. 827, Elsevier Science B.V.

Kumar et al., "The first analogues of LNA (Locked Nucleic Acids): phosphorothioate-LNA and 2'-thio-LNA," *Bioorganic and Medicinal Chemistry Letters*, Aug. 18, 1998, pp. 2219-2222, vol. 8, No. 16, Elsevier Science Ltd.

Egholm et al., "Peptide nucleic acids (PNA). Oligonucleotide analogues with an achiral peptide backbone," *Journal of the American Chemical Society*, 1992, pp. 1895-1897, vol. 114, American Chemical Society, USA.

Chevalier et al., "Biotin and digoxigenin as labels for light and electron microscopy in situ hybridization probes: Where do we stand?," *The Journal of Histochemistry and Cytochemistry*, 1997, pp. 481-491, vol. 45, No. 4, The Histochemical Society, Inc.

International Search Report issued in International Application No. PCT/FR2008/051012 on Feb. 25, 2009.

Aug. 9, 2010 International Search Report issued in International Patent Application No. PCT/FR2009/052458 (with translation).

(Continued)

Primary Examiner — Suryaprabha Chunduru
(74) Attorney, Agent, or Firm — Oliff PLC

(57) ABSTRACT

A cartridge that can be positioned inside an air collection component and receive a component for recovering nucleic acids is described, the cartridge being substantially cylindrical and containing a microorganism retaining zone, the retaining zone containing a microorganism lysis mechanism. Also described is a device for collecting microorganisms contained in the air and a device for microorganism lysis.

34 Claims, 10 Drawing Sheets

(56) References Cited

FOREIGN PATENT DOCUMENTS

| WO | WO 2006/117676 A2 | | 11/2006 |
|----|-------------------|---|---------|
| WO | WO 2006117676 A2 | * | 11/2006 |
| WO | WO 2008/104916 A2 | | 9/2008 |

OTHER PUBLICATIONS

Aug. 9, 2010 Written Opinion of the International Searching Authority issued in International Patent Application No. PCT/FR2009/052458 (with translation).

U.S. Appl. No. 13/129,997, filed May 18, 2011 in the name of Broyer et al.

Mar. 20, 2013 Office Action issued in U.S. Appl. No. 13/129,997.

* cited by examiner

DEVICE FOR THE LYSIS OF MICROORGANISMS PRESENT IN AN ENVIRONMENTAL OR CLINICAL SAMPLE AND THE EXTRACTION OF NUCLEIC ACIDS FROM SAID MICROORGANISMS FOR ANALYSIS

The technical field of the present invention is that of biological analysis. More particularly, the present invention relates to a device for the lysis of microorganisms present in an environmental sample, such as an air sample, or a clinical sample.

For several years, a resurgence in nosocomial infections in hospitals has been observed. These infections are explained by the contamination of hospitalized, and therefore by definition immunodepressed, individuals with pathogenic microorganisms present in the hospital environmental sphere, which have not been destroyed despite the always great care given to the disinfection of instruments and surfaces and to air treatment. With regard to these increasingly common cases of environmental microbiological contamination, the development of devices and methods for improving and facilitating environmental controls has come to represent major stakes for healthcare professionals.

In addition to the problem of nosocomial infections, the controlling of environmental conditions has also over the past several years become a recurrent concern in the industrial environment, in particular the food-processing industries or the pharmaceutical or cosmetics industries. In the food-processing industries, the disastrous consequences to consumer health that the contamination of products, or even of starting materials, with a pathogenic microorganism can have are known. Indeed, food poisoning due to bacteria such as those of the *Listeria* or *Salmonella* genus is today a common occurrence. The controlling of air quality is also a key process in the quality approach of the pharmaceutical or cosmetics industries.

Moreover, these controls must meet an increasingly high level of requirement owing to increasingly strict regulations.

Among the tools available to health professionals or manufacturers for carrying out environmental controls, aerobiocollectors are solutions of choice for detecting microorganisms in the air. These devices are placed at appropriate sites on the premises where it is desired to measure the aerobiocontamination. They are generally constituted of an air collector coupled to a culture medium. The air collected by the air collector comes into contact with the culture medium, the microorganisms possibly contained in the collected air becoming deposited on the culture medium. The culture medium is then recovered and placed in an incubator in order to promote growth of the microorganisms. It is thus possible to detect and identify said microorganisms by means of conventional microbiology techniques.

These devices nevertheless have a major drawback which is linked to the technology used. This drawback is the time required to obtain the result of the analysis. This is because the use of conventional microbiology, in particular bacteriology, techniques means that incubation times necessary for cell growth, or even times for phases of re-inoculation on specific culture media so as to enable identification, have to be adhered to. It follows that the time required to obtain a result is relatively long, indeed even too long, when the intention is to detect and identify a pathogenic organism responsible for a nosocomial infection or for food poisoning.

Another drawback of this type of device is that the use of culture media, while making it possible to discriminate between bacterial genera and species, does not generally make it possible to discriminate between the strains of the same bacterial species. Now, it is known that the pathogenicity of a microorganism can vary significantly according to the strain under consideration.

There are, moreover, devices for recovering particles present in the air, in particular microorganisms. Document GB-2 254 024 thus describes a device for collecting the particles contained in the air, the principle of which is based on the cyclone effect. While such a device is found to be suitable for collecting the particles contained in the air, including the microorganisms, it is in no way studied for treating the sample thus obtained, in particular for extracting the genetic material intended to be used for the analysis.

More generally, the most relevant techniques in terms of identifying microorganisms and/or of rapidity of providing results, whether with respect to clinical or environmental samples, are without any doubt the molecular diagnostics techniques. These techniques, based on analyzing the genetic material of microorganisms, and in particular certain specific sequences of interest, make it possible to obtain a very precise identification of the microorganisms in a record time, since they make it possible to do away with the culture steps.

Nevertheless, the use of such techniques presents a certain number of limits, among which the most important is the potential limited amount of microorganisms present in the air and therefore recoverable for carrying out the analysis. In fact, it is known that environmental samples, but also some clinical samples, have relatively low amounts of microorganisms. It follows that the amount of genetic material obtained from this starting material is small. The effectiveness of the technique used to extract the nucleic acids, in terms of yield, then becomes an essential parameter.

Moreover, most of the existing techniques for the lysis of microorganisms are long, requiring the involvement of qualified staff to carry out the manual steps.

Document WO-A-2005/038025 describes a method for the extraction of nucleic acids from microorganisms taken in particular from the air. This method consists in performing three different lysis methods, namely chemical lysis, thermal shock lysis and mechanical lysis. While such a method without doubt makes it possible to optimize the nucleic acid extraction yield and therefore to increase the amount of genetic material available for analysis, it nevertheless remains the case that this yield is still dependent on the amount of microorganisms recovered. However, there is nothing described in this document for optimizing the recovery of said microorganisms.

Document U.S. Pat. No. 5,707,861 describes a device for disintegrating living cells of the microorganism type. This device makes it possible to lyze the cells by using not only glass beads but also the effect of vibration due to the gap that exists between the tubes containing the microorganisms and the holes of the holder carrying said tubes. Thus, such a device makes it possible to optimize the cell lysis and therefore to optimize the extraction of the genetic material. Such a device and the method used by the latter present the same limits as those mentioned above, namely that they remain dependent on the amount of microorganisms recovered. Moreover, they have the additional drawback of having to subsequently carry out a nucleic acid concentration step in order to isolate said nucleic acids from the cell debris. Finally, they require manual recovery of the nucleic acids, at the end of the concentration step.

These problems also arise with the device described in document U.S. Pat. No. 5,567,050.

Systems that are more integrated have also been described. Thus, document WO-A-2004/018704 describes a device and a method using the PCR (Polymerase Chain Reaction) amplification technique for collecting microorganisms in the air and identifying them. This system is especially suitable for combating attempted biological contamination attacks in mail sorting centers. This system is made up of an air collection device placed along the mail transport circuit, a device for filtering/separating the particles by means of a cyclone effect, a device for concentrating/recovering the particles in a liquid sample, and a device for transferring a fraction of the sample to a GeneXpert™ PCR analysis cartridge from the company Cepheid. The cartridge is then transferred manually to an independent automated biological analysis device in order to identify the microorganism(s) collected from the air.

While this system makes it possible to solve many of the technical problems linked to the devices and methods described above, it nevertheless has major drawbacks. The first of these drawbacks is that the system for treating the sample (collection, separation, concentration/recovery) prior to transfer to the analytical cartridge is relatively complex and cumbersome. A second drawback is that the microorganisms collected are recovered in a liquid sample of which only one fraction is analyzed. This means that the risk of not recovering all the microorganisms and therefore all the nucleic acids is very high, greatly limiting the relevance of the analysis. Moreover, despite its complexity, this system requires the manual transfer of the cartridge to the GeneXpert™ automated analysis device.

Thus, a first objective of the present invention is to provide a device and a method for universal lysis, which are effective both for environmental samples and for clinical samples, for a large diversity of microorganisms, whether they are bacteria, viruses or else fungi, possibly in the vegetative state or in the form of spores.

Another objective of the present invention is to provide a device capable of effectively lyzing said microorganisms contained in an environmental sample such as the air, or in a clinical sample, in order to extract the nucleic acids therefrom and to recover said nucleic acids for analysis, in an integrated manner.

Another objective of the present invention is to provide a device capable of collecting all the microorganisms contained in an air sample.

Another objective of the present invention is to provide a device having a simple design.

Another objective of the present invention is to provide an excessively compact device.

Another objective of the present invention is to provide a closed device in which the various steps stated above take place without any risk of outside contamination.

Another objective of the present invention is to provide a device in which said steps take place without transfer of the sample by the operator, thereby preventing contamination thereof.

Finally, another objective of the present invention is to provide a device capable of providing target nucleic acids in a buffer that can be directly used in molecular diagnostics steps comprising, for example, amplification and detection steps, without additional pretreatment steps such as centrifugation or filtration.

These objectives, among others, are achieved by virtue of the present invention which relates firstly to a cartridge which can be positioned inside an air collection means and receive a means for recovering nucleic acids, said cartridge being substantially cylindrical and comprising a microorganism retaining zone, said retaining zone comprising microorganism lysis means.

Advantageously, the microorganism retaining zone comprises a material capable of retaining the microorganisms, of keeping the lysis means in place and of dissolving in the presence of a liquid. The material is preferably a gelled material.

The gelled material may advantageously be a microorganism culture medium.

According to one variant of the device, the latter comprises a means for connection to an analyzing device.

Preferably, the lysis means are constituted of beads. Even more preferably, the diameter of the beads is between 200 and 600 µm.

The invention also relates to a device for collecting microorganisms contained in the air, said device comprising:
  an air collection means, comprising an upper element comprising an air inlet duct and a lower element comprising an air outlet duct, it being possible for said upper and lower elements to be interlocked with one another such that a current of air can be created inside said air collection means;
  a substantially cylindrical cartridge comprising a microorganism retaining zone, said retaining zone comprising microorganism lysis means, said cartridge being positioned inside said air collection means.

The air collection means is capable of being connected to an air recycling circuit.

The invention also relates to a device for microorganism lysis, with the aim of isolating the nucleic acids from said microorganisms, said device comprising:
  a cartridge according to the invention, said cartridge comprising microorganisms placed in the microorganism retaining zone;
  a substantially cylindrical means for recovering nucleic acids, that can be fitted into the cartridge, said recovering means cooperating with the microorganism lysis means in order to lyze said microorganisms and enable release of the nucleic acids.

Advantageously, the means for recovering nucleic acids comprises a means for drawing up/delivering liquid.

Notably, the means for recovering nucleic acids also comprises a liquid storage zone.

According to one preferred embodiment, the internal diameter of the cartridge is greater than the external diameter of the means for recovering nucleic acids, such that, when the means for recovering nucleic acids is fitted into the cartridge, the distance separating the internal wall of the cartridge from the external wall of the means for recovering nucleic acids is sufficiently large to allow the lysis means to sit in this interstitial space and sufficiently small for the lysis means to be in contact with one or other of said walls.

The invention also relates to a method for concentrating microorganisms contained in the air, said method comprising the steps consisting in:
  a) placing a cartridge inside the air collection means, such that the retaining zone, inside said cartridge, is in communication with the air inlet duct of the air collection means,
  b) causing air to enter said air collection means by any appropriate means,
  c) concentrating the microorganisms contained in the air in the retaining zone of the cartridge.

According to one particular embodiment, it also comprises a step d) consisting in growing the microorganisms in the retaining zone.

Advantageously, the microorganisms are retained on the lysis means present in the retaining zone.

The invention also relates to a method for the lysis of microorganisms contained in the air, said method comprising the steps consisting in:
  a) placing a cartridge inside the air collection means, such that the retaining zone, inside said cartridge, is in communication with the air inlet duct of the air collection means,
  b) causing air to enter said air collection means by any appropriate means,
  c) concentrating the microorganisms contained in the air, in the retaining zone of the cartridge,
  d) removing the cartridge from the air collection means,
  e) placing the means for recovering nucleic acids in the cartridge, introducing a liquid of interest into the cartridge, which leads to the lysis means located in the microorganism retaining zone of the cartridge being placed in suspension, and
  g) mechanically lyzing the microorganisms by rotating the means for recovering nucleic acids, inside the cartridge, said means for recovering nucleic acids rotating the lysis means on which the microorganisms are retained.

The invention also relates to a method for the lysis of microorganisms contained in the air, said method comprising the steps consisting in:
  a) placing a cartridge inside the air collection means, such that the retaining zone, inside said cartridge, is in communication with the air inlet duct of the air collection means,
  b) causing air to enter said air collection means by any appropriate means,
  c) concentrating the microorganisms contained in the air, in the retaining zone of the cartridge,
  d) removing the cartridge from the air collection means,
  e) fitting the means for recovering nucleic acids into the cartridge,
  f) causing the delivery of a liquid of interest previously placed in the storage zone of the means for recovering nucleic acids, said delivery being obtained by means of the drawing up/delivering means of the means for recovering nucleic acids, the liquid thus delivered filling the interstitial space located between the means for recovering nucleic acids and the cartridge, which leads to the lysis means located in the microorganism retaining zone of the cartridge being placed in suspension, said lysis means coming to sit between the vertical internal wall of the cartridge and the vertical external wall of the means for recovering nucleic acids, and
  g) mechanically lyzing the microorganisms by rotating the means for recovering nucleic acids, inside the cartridge, said means for recovering nucleic acids rotating the lysis means on which the microorganisms are retained.

Another subject of the invention concerns a method for the extraction of nucleic acids from microorganisms contained in the air, said method comprising the steps consisting in:
  a) placing a cartridge inside the air collection means, such that the retaining zone, inside said cartridge, is in communication with the air inlet duct of the air collection means,
  b) causing air to enter said air collection means by any appropriate means,
  c) concentrating the microorganisms contained in the air, in the retaining zone of the cartridge,
  d) removing the cartridge from the air collection means,
  e) placing the means for recovering nucleic acids in the cartridge,
  f) introducing a liquid of interest into the cartridge, which leads to the lysis means located in the microorganism retaining zone of the cartridge being placed in suspension, and
  g) mechanically lyzing the microorganisms by rotating the means for recovering nucleic acids, inside the cartridge, said means for recovering nucleic acids rotating the lysis means on which the microorganisms are retained, and
  h) drawing up the liquid of interest containing the nucleic acids of said microorganisms, released during the lysis.

The invention also relates to a method for the extraction of nucleic acids from microorganisms contained in the air, said method comprising the steps consisting in:
  a) placing a cartridge inside the air collection means, such that the retaining zone, inside said cartridge, is in communication with the air inlet duct of the air collection means,
  b) causing air to enter said air collection means by any appropriate means,
  c) concentrating the microorganisms contained in the air, in the retaining zone of the cartridge,
  d) removing the cartridge from the air collection means,
  e) fitting the means for recovering nucleic acids into the cartridge,
  f) causing the delivery of a liquid of interest previously placed in the storage zone of the means for recovering nucleic acids, said delivery being obtained by means of the drawing up/delivering means of the means for recovering nucleic acids, the liquid thus delivered filling the interstitial space located between the means for recovering nucleic acids and the cartridge, which leads to the lysis means located in the microorganism retaining zone of the cartridge being placed in suspension, said lysis means coming to sit between the vertical internal wall of the cartridge and the vertical external wall of the means for recovering nucleic acids,
  g) mechanically lyzing the microorganisms by rotating the means for recovering nucleic acids, inside the cartridge, said means for recovering nucleic acids rotating the lysis means on which the microorganisms are retained, thus releasing the nucleic acids from said microorganisms, and
  h) causing the liquid of interest in the storage zone of the means for recovering nucleic acids to be drawn up, said drawing up being obtained by means of the drawing up/delivering means of the means for recovering nucleic acids, the liquid of interest thus drawn up containing the nucleic acids of said microorganisms, released during the lysis.

These extraction methods preferentially comprise an additional step d') consisting in growing the concentrated microorganisms in the retaining zone of the cartridge.

This growing is obtained by incubation of the cartridge in an incubator for a period of time ranging from 2 to 24 hours.

Another subject of the invention concerns a method for the lysis of microorganisms contained in the air, said method comprising the steps consisting in:
  a) obtaining a cartridge in which microorganisms are placed in the vicinity of the retaining zone,
  b) fitting the means for recovering nucleic acids into the cartridge,
  c) causing the delivery of a liquid of interest previously placed in the storage zone of the means for recovering nucleic acids, said delivery being obtained by means of the drawing up/delivering means of the means for recovering nucleic acids, the liquid thus delivered filling the interstitial space located between the means for recovering nucleic acids and the cartridge, which leads to the lysis means located in the microorganism retaining zone of the cartridge being placed in suspension, said lysis means coming to sit between the vertical internal wall of the cartridge and the vertical external wall of the means for recovering nucleic acids, and d) mechanically lyzing the microorganisms by rotating the means for recovering nucleic acids, inside the cartridge, said means for recovering nucleic acids rotating the lysis means on which the microorganisms are retained.

Another subject of the invention concerns a method for the lysis of microorganisms, said method comprising the steps consisting in:
a) obtaining a cartridge in which microorganisms are concentrated in the retaining zone,
b) placing the means for recovering nucleic acids in the cartridge,
c) introducing a liquid of interest into the cartridge, which leads to the lysis means located in the microorganism retaining zone of the cartridge being placed in suspension, and
d) mechanically lyzing the microorganisms by rotating the means for recovering nucleic acids, inside the cartridge, said means for recovering nucleic acids rotating the lysis means on which the microorganisms are retained.

Another subject of the invention concerns a method for the extraction of nucleic acids from microorganisms, said method comprising the steps consisting in:
a) obtaining a cartridge in which microorganisms are concentrated in the retaining zone,
b) fitting the means for recovering nucleic acids into the cartridge,
c) causing the delivery of a liquid of interest previously placed in the storage zone of the means for recovering nucleic acids, said delivery being obtained by means of the drawing up/delivering means of the means for recovering nucleic acids, the liquid thus delivered filling the interstitial space located between the means for recovering nucleic acids and the cartridge, which leads to the lysis means located in the microorganism retaining zone of the cartridge being placed in suspension, said lysis means coming to sit between the vertical internal wall of the cartridge and the vertical external wall of the means for recovering nucleic acids,
d) mechanically lyzing the microorganisms by rotating the means for recovering nucleic acids, inside the cartridge, said means for recovering nucleic acids rotating the lysis means on which the microorganisms are retained, thus releasing the nucleic acids from said microorganisms, and
e) causing the liquid of interest in the storage zone of the means for recovering nucleic acids to be drawn up, said drawing up being obtained by means of the drawing up/delivering means of the means for recovering nucleic acids, the liquid of interest thus drawn up containing the nucleic acids of said microorganisms, released during the lysis.

Another subject of the invention concerns a method for the extraction of nucleic acids from microorganisms, said method comprising the steps consisting in:
a) obtaining a cartridge in which microorganisms are concentrated in the retaining zone,
b) placing the means for recovering nucleic acids in the cartridge,
c) introducing a liquid of interest into the cartridge, which leads to the lysis means located in the microorganism retaining zone of the cartridge being placed in suspension, and
d) mechanically lyzing the microorganisms by rotating the means for recovering nucleic acids, inside the cartridge, said means for recovering nucleic acids rotating the lysis means on which the microorganisms are retained, and
e) drawing up the liquid of interest containing the nucleic acids of said microorganisms, released during the lysis.

The invention also concerns a method for the lysis of microorganisms, said method comprising the steps consisting in:
a) introducing a liquid sample containing said microorganisms into a cartridge according to the invention, in the vicinity of the retaining zone, such that said liquid sample leads to the lysis means located in said microorganism retaining zone of the cartridge being placed in suspension,
b) placing the means for recovering nucleic acids in the cartridge,
c) mechanically lyzing the microorganisms by rotating the means for recovering nucleic acids, inside the cartridge, said means for recovering nucleic acids rotating the lysis means on which the microorganisms are retained.

The term "liquid sample" is intended to mean any liquid sample that may contain microorganisms. It may be a liquid sample of human or animal origin. This sample may be, for example, a urine sample, a whole blood sample, a plasma sample or a sample of any other bodily fluid. The liquid sample may be of food origin, such as a drink. It may also be of environmental origin, such as water. Moreover, the liquid sample may also be a "transfer" liquid, in which possible microorganisms contained on a surface-sampling device, of the swab type, such as those sold by the company Copan, under the name flockedSWABS, have been resuspended by agitation of said swab in said transfer liquid.

In addition, the invention concerns a method for the extraction of nucleic acids from microorganisms, said method comprising the steps consisting in:
a) introducing a liquid sample containing said microorganisms into a cartridge according to the invention in the vicinity of the retaining zone, such that said liquid sample leads to the lysis means located in said microorganism retaining zone of the cartridge being placed in suspension,
b) placing the means for recovering nucleic acids in the cartridge,
c) mechanically lyzing the microorganisms by rotating the means for recovering nucleic acids, inside the cartridge, said means for recovering nucleic acids rotating the lysis means on which the microorganisms are retained,
d) drawing up the liquid of interest containing the nucleic acids of said microorganisms, released during the lysis.

Another subject of the invention concerns, in addition, a method for identifying one or more microorganisms, comprising the steps consisting in:
a) isolating the nucleic acids from the microorganisms contained in said sample by means of the device according to the invention,
b) identifying the microorganism(s) thus isolated.

According to one advantageous variant of the method of identification according to the invention, said method also comprises an intermediate step consisting in purifying the nucleic acids. This purification step makes it possible to separate the nucleic acids from the other cell constituents released in the lysis step. This step generally makes it possible to concentrate the nucleic acids, and can be adapted for the purification of DNA or of RNA. By way of example, it is possible to use magnetic particles optionally coated with oligonucleotides, by adsorption or covalence (in this respect, see patents U.S. Pat. Nos. 4,672,040 and 5,750,338), and thus to purify the nucleic acids which are bound to these magnetic particles, by means of a washing step. This nucleic acid purification step is particularly advantageous if the intention is to subsequently amplify said nucleic acids. One particularly advantageous embodiment of these magnetic particles is described in patent applications: WO-A-97/45202 and WO-A-99/35500. Another advantageous example of a method for purifying nucleic acids is the use of silica, either in the form of a column, or in the form of inert particles (Boom R. et al., J. Clin. Microbiol., 1990, n° 28(3), p. 495-503) or magnetic particles (Merck: →MagPrep®Silica, Promega: MagneSil™ Paramagnetic particles). Other very widely used methods are based on ion exchange resins in a column or in a paramagnetic particulate format (Whatman: DEAE-Magarose) (Levison P R et al., J. Chromatography, 1998, p. 337-344). Another method, which is very relevant but not exclusive for the invention, is that of adsorption onto a metal oxide support (the company Xtrana: Xtra-Bind™ matrix).

In particular, the identification step comprises the substeps consisting in:
a) specifically amplifying the isolated nucleic acids,
b) detecting the nucleic acids thus amplified.

According to one preferential variant of the method of identification, the identification step is carried out in an identification device in fluid communication with the cartridge of the device according to the invention.

Thus, the isolated nucleic acids are transferred from the means for recovering nucleic acids, of the device according to the invention, to the identification device.

The transfer of the nucleic acids is advantageously obtained by delivery of the liquid of interest containing the nucleic acids, said liquid of interest being contained in the storage zone of the means for recovering nucleic acids, by means of the drawing up/delivering means of the means for recovering nucleic acids.

The microorganisms are taken from the group comprising bacteria, viruses, yeasts, molds and parasites.

The samples from which the microorganisms are isolated are of environmental origin. Thus, they may be an air sample or a liquid sample, such as water; or surface samples. The samples may also be of clinical origin, i.e. any sample of human or animal origin, capable of being the subject of an analysis for searching for and identifying a microorganism, optionally a pathogenic microorganism.

The presence of the target nucleic acids is demonstrated by the visualization of hybridization reactions. The term "hybridization reaction" is intended to mean any reaction between a capture nucleic acid and a target nucleic acid which has been isolated or generated by means of a step of transcription, of reverse transcription or of amplification of NASBA (Nucleic Acid Sequence Based Amplification) or PCR (Polymerase Chain Reaction) type.

The term "nucleic acid" is intended to mean oligonucleotides, deoxyribonucleic acids and ribonucleic acids, and also derivatives thereof. The term "oligonucleotide" denotes a series of at least two natural or modified nucleotides (deoxyribonucleotides or ribonucleotides, or both) capable of hybridizing, under suitable hybridization conditions, with an at least partially complementary oligonucleotide. The term "modified nucleotide" is intended to mean, for example, a nucleotide comprising a modified base and/or comprising a modification at the level of the internucleotide bond and/or at the level of the backbone. By way of example of a modified base, mention may be made of inosine, methyl-5-deoxycytidine, dimethylamino-5-deoxyuridine, diamino-2,6-purine and bromo-5-deoxyuridine.

In order to illustrate a modified internucleotide bond, mention may be made of phosphorothioate, N-alkylphosphoramidate, alkylphosphonate and alkylphosphodiester bonds.

Alpha-oligonucleotides such as those described in FR-A-2 607 507, LNAs such as phosphorothioate-LNA and 2'-thio-LNA described in Bioorganic & Medicinal Chemistry Letters, Volume 8, Issue 16, 18 Aug. 1998, pages 2219-2222, and PNAs which are the subject of the article by M. Egholm et al., J. Am. Chem. Soc. (1992), 114, 1895-1897, are examples of oligonucleotides made up of nucleotides of which the backbone is modified.

The hybridization reactions can be visualized by any detection means such as direct or indirect means.

In the case of direct detection, i.e. without going through labeling, the hybridization reactions are observed by plasmon resonance or by cyclic voltametry on an electrode bearing a conductive polymer.

In the case of indirect detection, i.e. by means of labeling, the labeling can be carried out either directly on the target nucleic acids, or by means of a prelabeled binding partner specific for said nucleic acids.

The expression "binding partner specific for the target nucleic acids" is intended to mean any partner capable of binding with the target nucleic acid, and examples that will be given are nucleic acids, oligonucleotides or polynucleotides and enzyme substrates.

The term "labeling" is intended to mean the attachment of a label capable of directly or indirectly generating a detectable signal. A nonlimiting list of these labels consists of: enzymes which produce a signal that can be detected, for example, by electrochemistry, colorimetry, fluorescence, luminescence, or enzymes such as horseradish peroxydase (HRP), alkaline phosphatase (ALP), α-galactosidase or glucose-6-phosphate dehydrogenase; enzyme inhibitors; enzyme cofactors; particles such as gold particles, magnetic lattices, liposomes; chromophores such as luminescent or coloring compounds, radioactive molecules such as $^{32}P$, $^{35}S$ or $^{125}I$, fluorescent molecules such as fluorescein, rhodamine, Alexa®, umbelliferone, luminol or phycocyanins. In the case of fluorescence, it may involve the fluorescent product of an enzyme-substrate reaction, a fluorophore-quencher combination, fluorescence quenching, or any other system based on fluorescence properties.

Indirect systems may also be used, for example involving another pair, the ligand/antiligand pair. Ligand/antiligand pairs are well known to those skilled in the art, and mention may, for example, be made of the following pairs: biotin/streptavidin, sugar/lectin, polynucleotide/sequence complementary to the polynucleotide. In this case, it is the ligand which carries the binding agent. The antiligand may be detectable directly via the labels described in the preceding paragraph, or may itself be detectable via a ligand/antiligand.

These indirect detection systems may, under certain conditions, result in amplification of the signal. This signal amplification technique is well known to those skilled in the art, and reference may be made to prior patent applications FR-A-2 781 802 or WO-A-95/08000 by the applicant or to the article J. Histochem. Cytochem. 45: 481-491, 1997.

The prelabeling of the target nucleic acids may be carried out by direct or indirect incorporation of label by means of a polymerase or by means of a kinase, randomly or specifically, at the ends, or by incorporation "within" the molecule.

The labeling of binding partners specific for target analytes is widely known to those skilled in the art and is described, for example, by Greg T. Hermanson in Bioconjugate Techniques, 1996, Academic Press Inc, 525B Street, San Diego, Calif. 92101 USA.

Depending on the type of labeling of the conjugate used, for instance using an enzyme, those skilled in the art will add reagents for visualizing the labeling. This step corresponds to the revealing. It is preceded by the use of a washing buffer which makes it possible to remove the fractions of analytes or of elements not involved in the reaction, or weakly or nonspecifically bound, in order to limit the background noise.

The objectives and advantages of the device according to the present invention will be understood more clearly in the light of the following example, which is in no way limiting, with reference to the drawing, in which.

Figure 1:
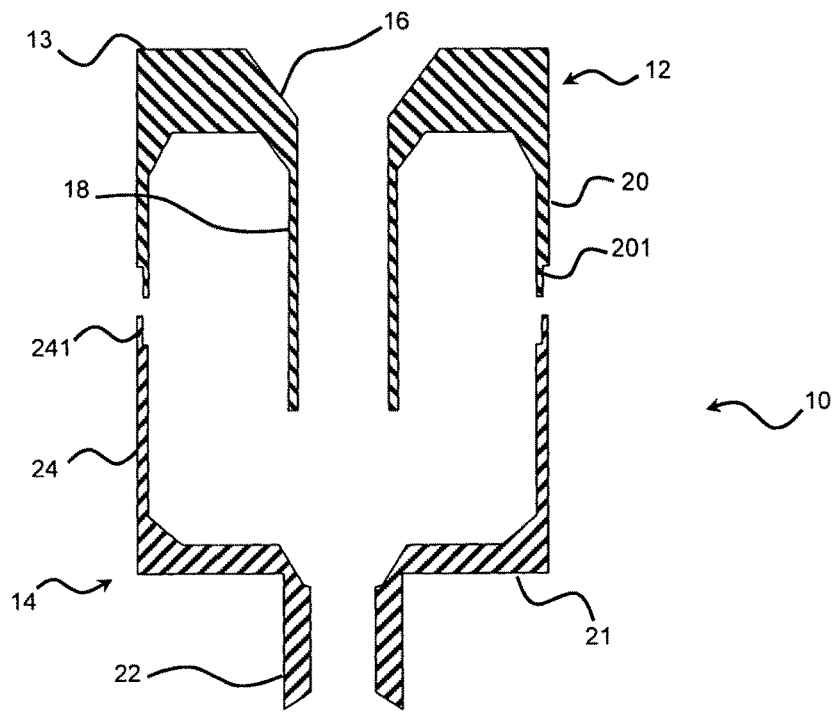
FIG. 1 represents an exploded view in longitudinal section of the air collection means, according to a first embodiment of the invention.

According to a first embodiment, the first element constituting the device according to the invention is an air collection means 10. This means is composed of an upper element 12 and of a lower element 14. The upper element 12 has a generally cylindrical shape. The lower end of this cylinder is free, whereas the upper end is partially closed off, by means of a horizontal wall 13. In its center, this wall 13 has an orifice extending inside the upper element 12, by means of a duct 18, the base of which is substantially conical in shape. This part in fact constitutes the duct for air inlet into the air collection means 10. According to one particular embodiment, this air inlet duct may be connected to a pipe of an air recycling circuit by any appropriate means.

The air collection means 10 may, for example, have an external diameter of between 10 and 40 mm, preferably 20 mm. The internal diameter of the air inlet duct is, for example, 6 mm.

This air collection means 10 may advantageously be made of a material that can be sterilized, in particular by autoclaving. It may thus be made of a metal, such as aluminum or steel. It may also be made of a polymer, such as poly(methyl methacrylate) (PMMA).

The lower end of the vertical circular wall 20 of the upper element 12 comprises, on its external face, a shoulder 201. This recess is made over the entire circumference of the wall 20. It is intended to facilitate the interlocking of the upper element 12 and the lower element 14.

The lower element 14 is also generally cylindrical in shape. The upper end of this cylinder is free, whereas the lower end is partially closed off, by a horizontal wall 21 comprising, in its center, a substantially cylindrical air outlet duct 22, the base of said duct being integral with the horizontal wall. The lower end of the duct 22 is free. This duct is in communication with the inside of the lower element 14, such that, when the upper element 12 and the lower element 14 of the air collection means 10 are interlocked, the duct 22 plays the role of an outlet duct for the air which was allowed into the air collection means 10, by means of the air inlet duct 18.

The upper end of the vertical circular wall 24 of the lower element 14 comprises, on its internal face, a shoulder 241. This shoulder is made over the entire circumference of the wall 24. It is also intended to facilitate the interlocking of the upper element 12 and the lower element 14, owing to the fact that the ends of the walls 20 and 24 have a cross section of complementary shape, facilitating the fitting together. It is important first of all for this interlocking to be reversible. Once fitted together, the elements 12 and 14 should be able to disengage from one another.

An alternative means of interlocking the elements 12 and 14 may be interlocking by screwing one element onto the other. To this end, the end of the wall of one of the elements 12 or 14 may carry a male thread and the end of the wall of the second element a corresponding female thread.

The important thing is that the collection means is hermetically closed, in order to prevent any parasitic entry of air.

According to one particular mode of use of the air collection means, the lower end of the air outlet duct 22 may be connected to an air suction pump (not represented) or any other equivalent pumping means. This pump makes it possible to suck the ambient air into the air collection means, when it is desired, for example, to perform an analysis of the ambient air in a given environment, such as a hospital room or a room for the production of pharmaceutical products or food-processing products. To this end, it may be preferable to have an autonomously operating pumping means.

Figure 2:
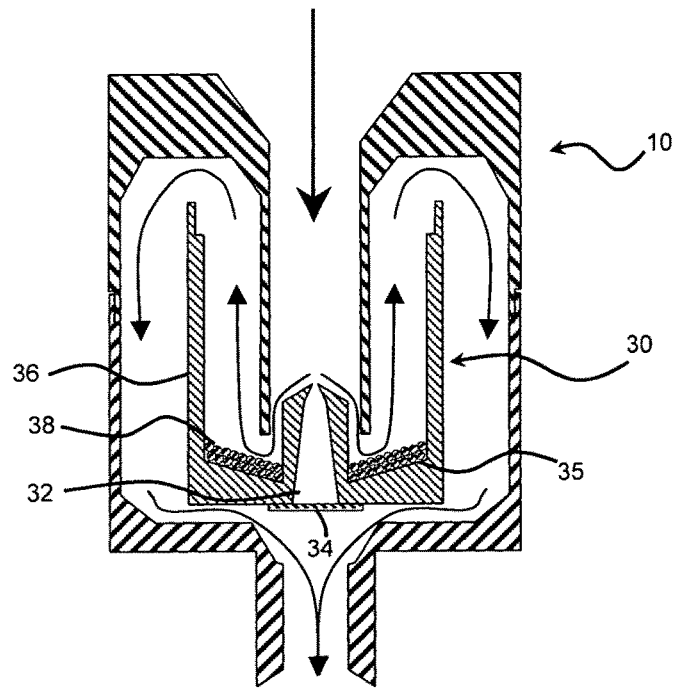
FIG. 2 represents a view in longitudinal section of the air collection means in which a cartridge has been placed, during the step of collecting the microorganisms, according to a first embodiment of the invention.
Figure 3:
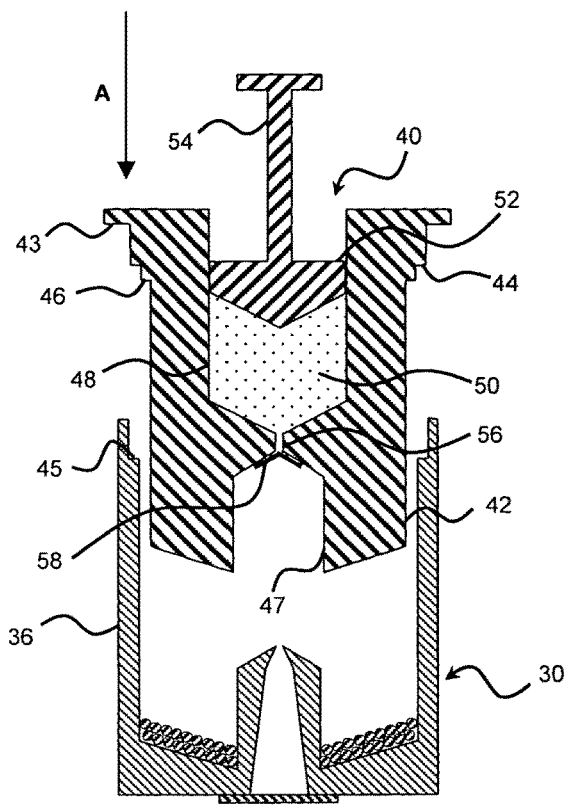
FIG. 3 represents a view in longitudinal section of the cartridge and of the means for recovering nucleic acids at an initial stage of the process for fitting said means inside the cartridge, according to a first embodiment of the invention.
Figure 4:
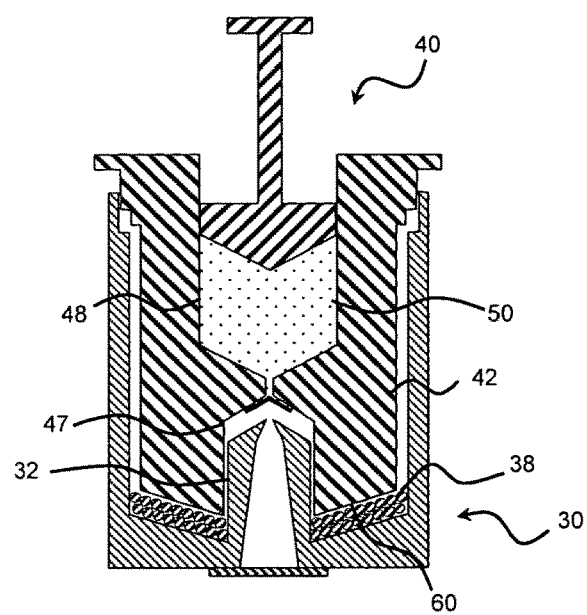
FIG. 4 represents a view in longitudinal section of the cartridge and of the means for recovering nucleic acids at an advanced stage of the process for fitting said means inside the cartridge, according to a first embodiment of the invention.

FIG. 2 represents the air collection means 10, during operation thereof, combined with a cartridge 30. As can be seen in this figure, the cartridge 30 is arranged inside the air collection means 10. To do this, the element 12 and 14 constituting the air collection means 10 are separated. The cartridge 30 is placed to bear in the lower element 14 of the air collection means 10. The upper elements 12 is then repositioned on the lower element 14 and these two means are interlocked. The assembly constituted of the air collection means 10 and the cartridge 30 is then either connected to a recycling circuit, or to a pumping device, in order to bring about circulation of the air inside the air collection means 10, as described above.

The cartridge 30 represented in FIG. 2, in longitudinal section, has the general shape of a cylinder with a substantially circular transverse section. The upper end of the cylinder is free, whereas the lower end is constituted of a wall, having, in its center, an orifice, there being, along the extension of said orifice, a duct 32 extending inside the cartridge 30. It is noted that the internal cross section of the duct tends to become smaller as one approaches the upper end of the duct. It is noted, moreover, that the lower end of the duct is closed off by a membrane 34, which plays the role of a septum. The material constituting the membrane 34 is suitable for being burst by simple pressure with a pointed object. This process is described below in relation to FIGS. 9 and 10. This material is, for example, a polyethylene terephthalate (PET) or a polycarbonate.

As can be seen in FIG. 2, the internal face of the lower wall 35 of the cartridge 30 is on a slant, the lowest point of the slope being in contact with the duct 32 and the highest point in contact with the vertical wall 36 of the cartridge 30. This wall 35 serves as a support for the lysis means 38 and constitutes the microorganism retaining zone. These lysis means are in this case constituted by beads of identical size. According to one preferred embodiment, these beads are made of glass. They could nevertheless be constituted of any other equivalent material, such as iron. These beads have a diameter advantageously of between 200 and 800 micrometers ($\mu$m).

According to one advantageous variant, the beads may be of different sizes. It may thus be particularly suitable to use a mixture of beads of diameter between 200 and 300 $\mu$m with beads of which the diameter is between 400 and 600 $\mu$m.

The beads are kept in place in the form of one or more superimposed layers by means of a gelled material, deposited in the form of a layer, in which the layer(s) of beads is (are) embedded. The gelled material should satisfy several constraints. The first is that it should be inert, so as not to influence the processes which are carried out inside the cartridge. The second is that it should have the capacity to dissolve in a liquid, in order to release the particles that it is trapping for the implementation of the microorganism lysis. Such a material may, for example, be agarose.

Alternatively, the gelled material may advantageously be a culture medium for the microorganisms. In fact, agar culture media have been conventionally used in the field of in vitro diagnostics for a very long time. The use of such a culture medium has several advantages. The main advantage is that it enables a growth phase for the microorganisms before lysis of the latter is carried out. Even though the device according to the invention seeks to meet a need linked to the rapid detection of pathogenic microorganisms, it nevertheless remains that a growth phase of a few minutes to a few hours would enable multiplication of the microorganisms, which has the direct effect of having a greater amount of nucleic acids. A second advantage of the use of culture media is that the latter can be selective for one or more given species. It follows that the use of such media can enable selective growth and therefore selective detection of certain pathogenic microorganisms to the detriment of other microorganisms that are of no interest, and that can possibly interfere in the analysis. Thus, it can be envisioned to have several specialized cartridges, each being suitable for the detection of a specific species of microorganism.

The dimensions of the cartridge 30 may, for example, be from 8 to 16 mm as regards the internal diameter, preferably 12 mm. The total thickness of the layers of beads is typically between 1 and 2 mm, which corresponds to an amount of glass beads of between 0.4 and 1 gram.

The cartridge 30 is advantageously made using an injection-molding technique. The material used is, for example, polypropylene, polystyrene, polycarbonate or PMMA.

When the circulation of air in the air collection means is initiated, the path followed by said air is represented by the arrows in FIG. 2. Thus, it is noted that the air enters the air collection means 10 via the air inlet duct 18. Since the duct 32 of the cartridge 30 is partially inserted into the air inlet duct 18, the air flow in the latter becomes converted, at the top of the duct 32, into a peripheral flow. This is explained by the fact that the upper end of the duct 32 is substantially conical in shape. Moreover, the presence of the membrane 34 at the base of the duct 32 prevents the air from penetrating into the duct 32, since the latter is very rapidly in a state of increased pressure. Since the interstitial space between the wall of the inlet duct 18 and the wall of the duct 32 narrows abruptly by virtue of the conical shape of the end of the duct 32, there is an acceleration of the peripheral air flow. It follows that the latter breaks on the upper layer of beads 38, leading, at this site, to the retention, by impaction, of the microorganisms transported in the air flow, at the surface of the gelled material or of the culture medium. Such a process is thus therefore relatively similar to that which occurs in aerobiocollectors.

The air, for its part, continues its route, drawn by the pumping means. It rises back up along the internal face of the vertical wall 36 of the cartridge 30, at the level of which it loses speed owing to widening of the circulation path. It redescends along the external face of this same wall and again becomes converted into a centralized flow at the entry of the air outlet duct 22, which escapes from the air collection means 10 via said air outlet duct.

The flow rate of air collected in the air collection means 10 may, for example, be between 20 and 100 liters/minute (l/min). It is advantageously 50 l/min.

Once the microorganism retaining/concentrating step inside the cartridge has been carried out, the latter is removed from the air collection means by unfastening the upper element 12 and lower element 14 of said means, either by dislocation or by unscrewing.

At this stage, there is the opportunity of incubating the cartridge in an incubator at 37° C., if it is desired to culture the microorganisms concentrated in said cartridge. As already explained above, this incubation generally lasts a few tens of minutes to a few hours, so as not to extend the analysis time too greatly. Nevertheless, if the obtaining of a result of analysis is not urgent, it may be envisioned to incubate the cartridge for a longer period of time more suitable to the constraints of bacterial growth, namely approximately twenty-four hours.

Similarly, it may also be envisioned to store the cartridge in an environment suitable for this storage, such as a cold room, if it is desired to defer the analysis.

According to one variant of the invention, the cartridge 30 may be provided directly placed in the air collection means 10. This type of presentation has the advantage of avoiding the user having to place the cartridge in the air collection means and therefore thus reducing the risks of contamination during this step. It is particularly advantageous, in this situation, for the air collection means 10 to be made of the same material as the cartridge 30, namely of polypropylene, polycarbonate or PMMA. Manufacture by injection-molding is then particularly suitable.

When the analysis is carried out, the cartridge 30 is interlocked with the means for recovering nucleic acids 40, as represented in FIG. 3. Said means is inserted into the cartridge via the free end of the latter, according to a vertical translational movement represented by the arrow A.

The means for recovering nucleic acids 40, represented in longitudinal section in FIG. 3, comprises a body 42 of generally cylindrical shape having a circular cross section. The body 42 has, on the upper part of its external wall, a shoulder 43, the function of which is to ensure that the cartridge 30-means for recovering nucleic acids 40 assembly is leaktight, when said means for recovering nucleic acids is completely inserted in the cartridge 30, by bearing against the upper end of the vertical wall 36 of the cartridge 30. The external wall of the body 42 has, moreover, several successive recesses in its top part. The recess 44 located under the shoulder 43 itself plays the role of a shoulder since it bears against the shoulder 45 made at the upper end of the vertical wall 36, when the means 40 is completely inserted into the cartridge 30, as represented in FIG. 5. The second recess 46 positioned under the recess 44 has, for its part, the function of enabling the diameter of the body 42 to be reduced, such that there remains an interstitial space between the external surface of the vertical wall of the body 42 and the internal surface of the vertical wall 36 of the cartridge 30. The role of this space will be explained below. Moreover, all these shoulders and recesses make it possible to reinforce the leaktightness of the assembly constituted of the cartridge 30 and the means for recovering nucleic acids 40.

At its base, the body 42 has, in the central position, a cavity 47 which is substantially cylindrical in shape with a circular cross section, the upper end of which is substantially conical in shape. Similarly, it also comprises a cavity 48 in its upper part, in the central position. This cavity 48, which is substantially cylindrical in shape with a circular cross section, the lower end of which is substantially conical in shape, constitutes a storage zone in which a liquid of interest 50 is placed. This liquid makes it possible to resuspend the glass beads 38, but also to recover the nucleic acids, once the microorganisms have been lyzed. It is therefore important for this liquid to be inert with respect, on the one hand, to the microorganisms and, on the other hand, to the nucleic acids, but also with respect to biological protocols. Thus, this liquid of interest is typically a buffer suitable for the implementation of biological protocols. The volume of liquid of interest contained in the cavity 47 may be between, for example, 0.1 and 0.4 milliliter (ml).

In order to enable the liquid of interest to play its role, the cavity 48 cooperates with a drawing up/delivering means constituted of a plunger 52 of which the shape is complementary to the lower part of the cavity 48 and an arm 54 in the vertical position, which is integral with the plunger 52, and which extends outside the cavity 48. The end of the arm opposite that attached to the plunger 52 may have a head of particular shape capable of engaging a means for actuating (not represented) the drawing up/delivering means translationally according to a substantially vertical movement. This actuating means is preferably an automated means.

The cavity 48 is in fluid communication with the cavity 47 by means of a channel 56, connecting the lower end of the cavity 48 to the upper end of the cavity 47. In FIG. 3, the channel 56 is closed off by means of a membrane 58 positioned at the upper end of the cavity 47, preventing emptying of the cavity 47. This membrane is also made of a material that can be perforated. In particular, this membrane may be perforated by means of the upper end of the duct 32 of the cartridge 30.

As shown in FIG. 4, the external shapes of the means for recovering nucleic acids 40 are perfectly complementary to the internal shapes of the cartridge 30. It follows that the means 40 sits perfectly inside the cartridge 30, the duct 32 playing the role of a guide by inserting itself into the cavity 47. The means 40 is positioned until the lower wall 60 of the means 40 is bearing against the beads 38.

At this stage, there is a pressure movement on the body 42 of the means for recovering nucleic acids and simultaneously on the drawing up/delivering means in accordance with the arrow B represented in FIG. 5. This translational movement of the drawing up/delivering means leads to the delivery of the liquid of interest 50 into the cavity 47 via the channel 56, and more particularly into the interstitial space between the internal wall of the cavity 47 and the external wall of the duct 32. This delivery is possible since the pressure exerted by the liquid on the membrane 58 leads to the perforation or the detachment of said membrane. The liquid of interest 50 then travels to the retaining zone of the cartridge where the glass beads 38 are located, and fills this zone, creating the suspending of the gelled material trapping the beads, such that the latter are entrained in the flow of liquid of interest, created by the drawing up/delivering means, to the interstitial space 62, between the means for recovering nucleic acids 40 and the cartridge 30. It should be noted that this interstitial space preferably has a width between 600 and 800 μm. This width is directly linked to the diameter of the beads 38 used. Specifically, the beads should be able to readily circulate in this space, but should also be able to be rotated by the means for recovering nucleic acids 40. To this end, the external vertical wall 64 of the body 42 preferably has a rough surface, which facilitates the rotating of the beads.

Figure 5:
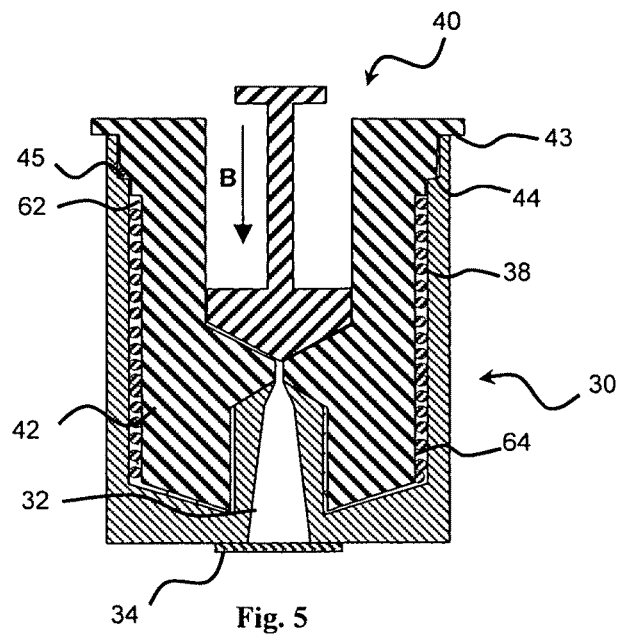
FIG. 5 represents a view in longitudinal section of the cartridge and of the means for recovering nucleic acids at the final stage of the process for fitting said means inside the cartridge, according to a first embodiment of the invention.

Once all the beads are positioned along the external vertical wall 64 of the body 42, the means for recovering nucleic acids can be completely inserted into the cartridge, thus generating the leaktightness of the assembly, by virtue in particular of the shoulders 43 and 44, which respectively bear against the end of the wall of the cartridge 30 and against the shoulder 45, as represented in FIG. 5.

Of course, the microorganisms retained both on the gelled material and on the beads are transferred into the interstitial space 62 in the same way as the beads 3, by the flow of the liquid of interest.

With regard to the transfer of the liquid of interest, it appears that the presence of the membrane 34 at the base of the duct 32 prevents the air contained in the duct 32 from being expelled when the liquid of interest is pushed into the channel 56. It follows that the pressure generated in the duct 32 by the trapped air prevents the liquid of interest from entering the duct, said liquid of interest therefore infiltrating the interstitial space between the internal wall of the cavity 47 and the external wall of said duct 32.

Figure 6:
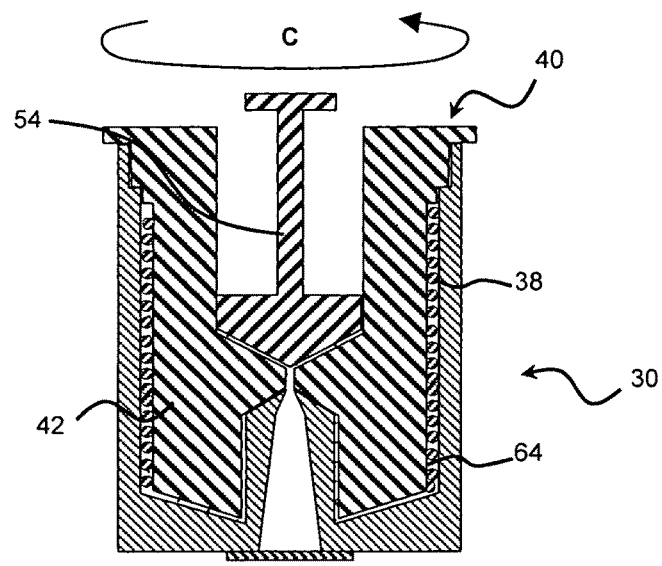
FIG. 6 represents a view in longitudinal section of the means for recovering nucleic acids, fitted into the cartridge, during the step of mechanical lysis of the microorganisms, according to a first embodiment of the invention.

Once the beads 38 are distributed along the external vertical wall 64 of the body 42 and the means for recovering nucleic acids 40-cartridge 30 assembly is interlocked, the lysis step per se is initiated. This step is represented in FIG. 6. As can be seen in this figure, the means for recovering nucleic acids 40 is rotated in the direction represented by the arrow C. For this, the body 42 of the means for recovering nucleic acids 40 is interlocked, by any suitable mechanical coupling means, with an automated device. Such a system makes it possible in particular to precisely adjust the speed of rotation.

It can nevertheless be envisioned to rotate the means for recovering nucleic acids manually. For this, gripping means (not represented) may be specifically provided on the upper part of the body 42. These gripping means can then be seized with one hand, while the cartridge 30 is held with the other hand.

By way of example, the speed of rotation values may be between 300 and 2000 rpm, preferably 1000 rpm.

The rotation time is, for its part, generally between 1 and 2 minutes.

It is quite obvious that the choice of these two parameters depends on the type of microorganisms that it is intended to lyze. Thus, in order to lyze yeasts of the *Saccharomyces cerevisiae* type, the optimal lysis conditions consist of a speed of rotation equal to 1000 rpm, for 2 minutes.

During this step, the beads 38 are rotated around the axis of symmetry by friction against the body 42 of the means for recovering nucleic acids. This double rotation leads to the mechanical lysis of the microorganisms which are trapped between the beads 38 and the body 42. This results in release of the nucleic acids into the liquid of interest.

Figure 7:
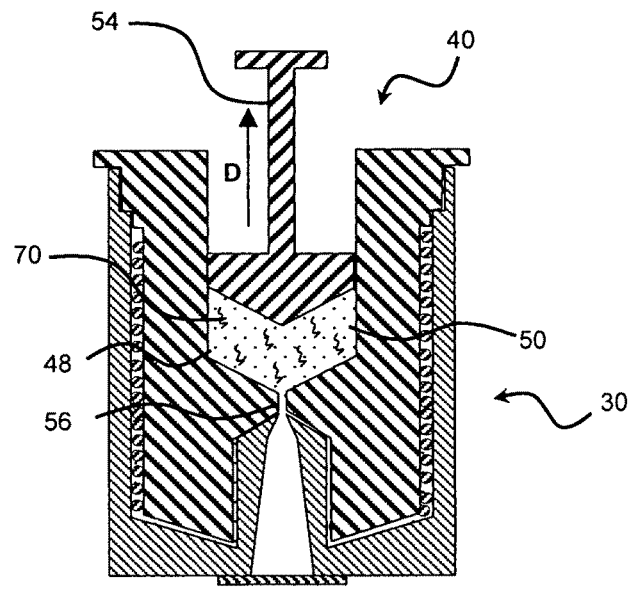
FIG. 7 represents a view in longitudinal section of the means for recovering nucleic acids, fitted into the cartridge, during the step of drawing the liquid of interest containing the nucleic acids up into the storage zone of the means for recovering nucleic acids, according to a first embodiment of the invention.
Figure 8:
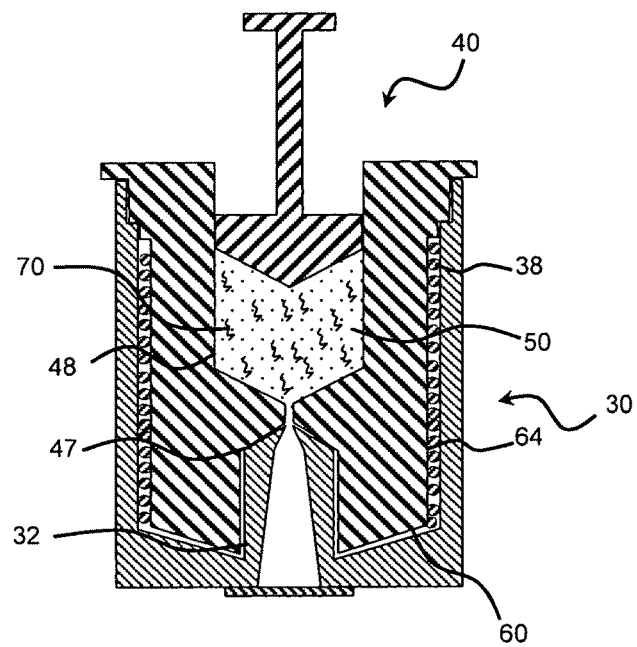
FIG. 8 represents a view in longitudinal section of the means for recovering nucleic acids, fitted into the cartridge, when all the liquid of interest containing the nucleic acids has been drawn up into the storage zone of the means for recovering nucleic acids, according to a first embodiment of the invention.

Once the lysis step has been completed and the nucleic acids released, the liquid of interest is drawn up into the cavity 48 by means of the drawing up/delivering means, as represented in FIG. 7. In detail, the drawing up/delivering means is moved by vertical translation according to the arrow D, by any suitable automatic or manual means of traction on the arm 54. This translational movement leads to the drawing up of the liquid of interest 50 into the cavity 48. During this drawing up, the liquid of interest follows the reverse path of that which it follows during its delivery prior to the lysis step. In particular, it progresses into the interstitial spaces between the means for recovering nucleic acids 40 and the cartridge 30, goes back up the channel 56 and ends up in the cavity 48. As can be seen in FIGS. 7 and 8, the liquid of interest which fills the cavity 48 is loaded with target nucleic acids 70 of the microorganisms.

Since the means for recovering nucleic acids 40 is entirely inserted into the cartridge 30, the interstitial space located between the lower wall 60 of said means 40 and the bottom of the cartridge, playing the role of microorganism retaining zone, freed of the beads, is not sufficient to allow the beads 38 to travel. It follows that the beads 38 remain positioned along the vertical wall 64 of the body 42.

Similarly, the interstitial space between the internal wall of the cavity 47 and the external wall of the duct 32 is particularly suitable for playing the role of a filter, in particular for retaining the cell debris produced during the lysis step. This is because, during the manufacture of the cartridge and of the means for recovering nucleic acids, the dimensions of said cartridge and said means for recovering nucleic acids can be adjusted in such a way that the size of this interstitial space is particularly well-controlled and optimizes the filtering effect.

Once all the liquid of interest has been drawn up into the cavity 48, it can be envisioned to transfer said liquid into a biological analysis device. This transfer may be carried out directly into the analyzing device or into a fluidic circuit of which the final element is the analyzing device.

When the liquid of interest is transferred directly into the device, it is envisioned that all the nucleic acid treatment steps for identifying the microorganism(s) be carried out in the device itself. Thus, it may be envisioned, for example, to carry out, in the device, the amplification of the target nucleic acids, the cleavage and the labeling of these target nucleic acids, and the detection thereof by hybridization with complementary sequences.

Figure 9:
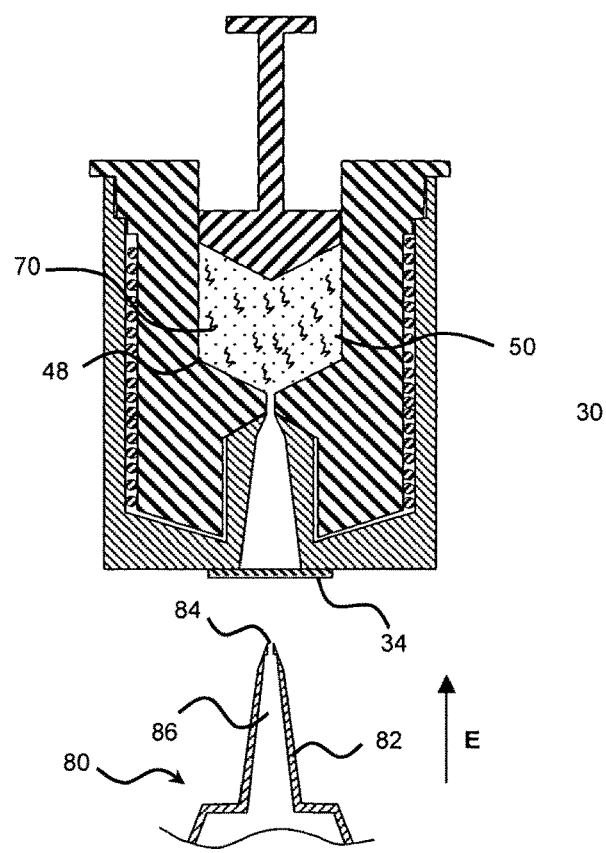
FIG. 9 represents a view in longitudinal section of the means for recovering nucleic acids, fitted into the cartridge, during the presentation of the means for identifying microorganisms, according to a first embodiment of the invention.
Figure 10:
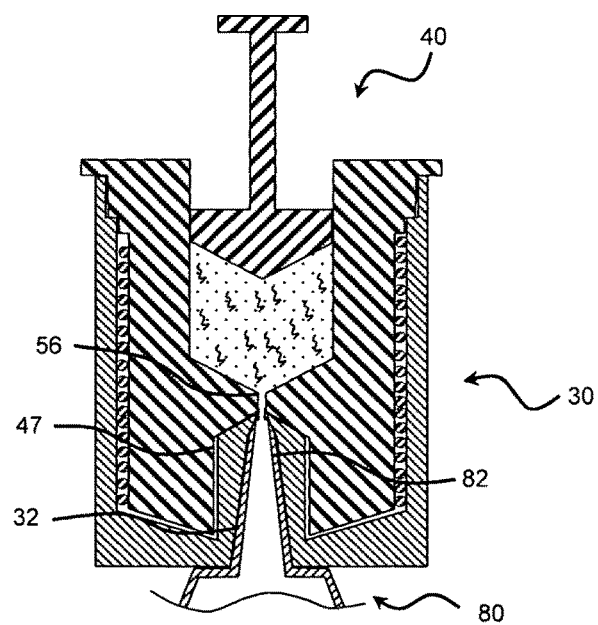
FIG. 10 represents a view in longitudinal section of the means for recovering nucleic acids, fitted into the cartridge, once the means for identifying microorganisms is in fluid communication with the cartridge, according to a first embodiment of the invention.

In FIG. 9, a fluidic analyzing device 80 is partially represented in longitudinal section. This device 80 comprises, in its upper part, a preferential zone 82 for fluidic connection to the means for recovering nucleic acids 40-cartridge 30 assembly. The preferential connection zone 82 is generally conical in shape, more particularly complementary to the shape of the duct 32. At its top, it has an aperture 84 for gaining access to the internal fluidic circuit 86 of the device 80. As represented in this FIG. 9, the fluidic analyzing device 80 is connected to the means for recovering nucleic acids 40-cartridge 30 assembly by bringing the preferential connection zone 82 up to the base of said assembly, in particular at the level of the membrane 34 closing off the duct 32, in accordance with the arrow E. Since the end of the preferential connection zone 82 is pointed, when the latter comes into contact with the membrane 34, it perforates said membrane, freeing the access to the duct 32. The analyzing device 80 is then inserted into the duct 32 until it is touching, i.e. until the external wall of the preferential connection zone is in contact with the internal wall of the duct 32, as represented in FIG. 10. When the analyzing device 80 is thus connected to the means for recovering nucleic acids 40-cartridge 30 assembly, it is noted that the end of the preferential connection zone 82 comes into contact with the lower end of the channel 56. It follows that the wall of the fluidic device 80, in the upper part of the preferential connection zone 82, cuts off the fluid communication between the channel 56 and the interstitial space between the internal wall of the cavity 47 and the external wall of the duct 32.

Figure 11:
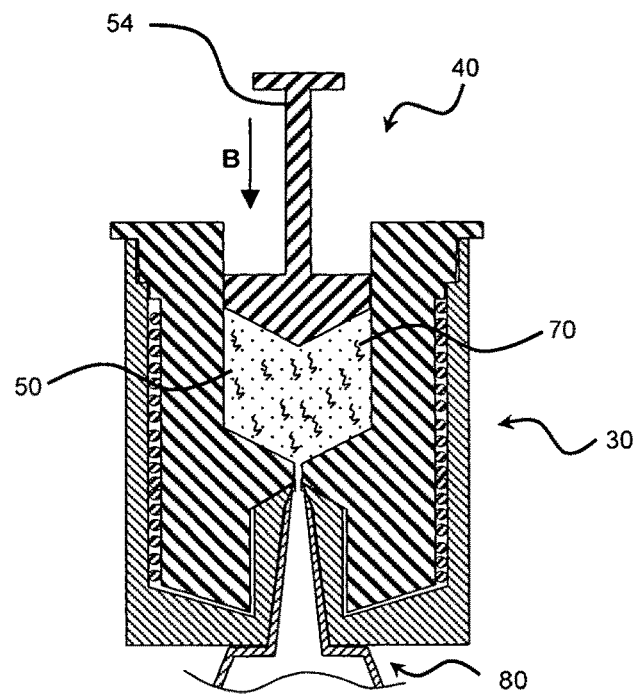
FIG. 11 represents a view in longitudinal section of the means for recovering nucleic acids-cartridge-means for identifying microorganisms assembly, in the initial phase of transfer of the liquid of interest containing the nucleic acids, into the means for identifying microorganisms, according to a first embodiment of the invention.

It follows that, when the operator wishes to transfer the liquid of interest 50 loaded with target nucleic acids 70 into the analyzing device 80, it is sufficient to exert, once again, a pressure on the arm 54 of the drawing up/delivering means, such that said means moves by vertical translation into the cavity 48, in accordance with the arrow B. This is represented in FIG. 11.

Figure 12:
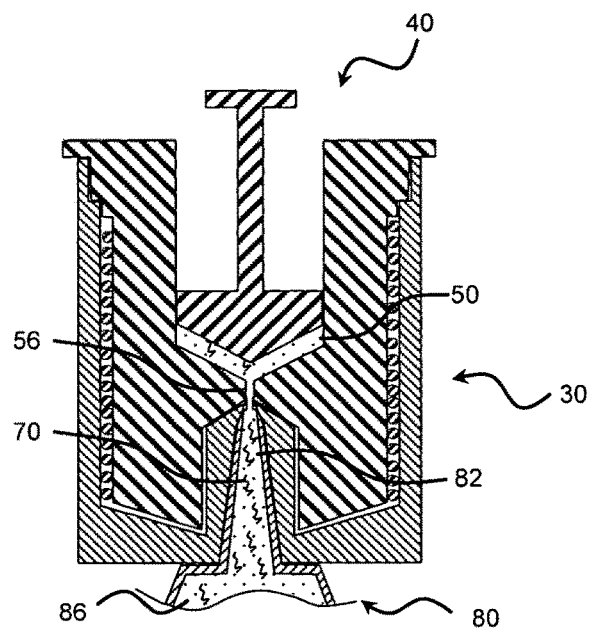
FIG. 12 represents a view in longitudinal section of the means for recovering nucleic acids-cartridge-means for identifying microorganisms assembly, after transfer of the liquid of interest containing the nucleic acids, into the means for identifying microorganisms, according to a first embodiment of the invention.

The moving of the drawing up/delivering means leads to the transfer of the liquid of interest 50 and of the nucleic acids 70 into the channel 56 connecting the cavity 48 to the cavity 47. Since the channel 56 is in direct fluid communication with the internal fluidic circuit 86 of the fluidic analyzing device 80 by means of the aperture 84 of the preferential connection zone 82, the liquid of interest is then transferred directly into the analyzing device 80, without any risk of said liquid coming into contact with the outside environment. There is also no risk of the liquid of interest escaping into the interstitial spaces between the means for recovering nucleic acids 40 and the cartridge 30, since any fluid communication between the channel 56 and the interstitial space between the internal wall of the cavity 47 and the external wall of the duct 32 is blocked. This is represented in FIG. 12.

Once all of the liquid of interest 50 and of the nucleic acids 70 have been transferred into the fluidic analyzing device 80, said device can be disengaged from the means for recovering nucleic acids 40-cartridge 30 assembly. Since the latter are used, they are disposed of. The fluidic analyzing device 80 is, for its part, subsequently used to carry out the identification of the microorganisms.

According to one advantageous embodiment, all the steps described above in relation to FIGS. 1 to 12, and in particular those linked to the microorganism lysis, the nucleic acid extraction and the transfer of said nucleic acids into the fluidic analyzing device, can be automated by means of an ad hoc system.

FIGS. 13 to 16 represent a second embodiment of the device according to the invention. The device under consideration has a simpler design than the device according to the first embodiment.

The device according to this second embodiment also comprises an air collection means 90. This means is composed of an upper element 92 and of a lower element 94. The upper element 92 is generally cylindrical in shape. The lower end of this cylinder is free, whereas the upper end is partially closed off, by means of a horizontal wall 93. This wall 93 has, in its center, an orifice extending into the upper element 92, by means of a duct 98, the base of which is substantially conical in shape. This part in fact constitutes the duct for inlet of air into the air collection means 90. According to one particular embodiment, this air inlet duct may be connected to a pipe of an air recycling circuit by any appropriate means.

In its lower part, the duct 98 comprises a screen 99. The function of this screen is to allow a homogeneous distribution of the air flow inside the air collection means 90.

The lower end of the vertical circular wall 100 of the upper element 92 comprises, on its external face, a shoulder 100$_1$. This recess is made over the entire circumference of the wall 100. It is intended to facilitate the fitting together of the upper element 92 and the lower element 94.

The lower element 94 is also generally cylindrical in shape. The upper end of this cylinder is free, whereas the lower end is partially closed off, by means of a horizontal wall 101 comprising, in its center, a substantially cylindrical air outlet duct 102, the base of said duct being integral with the horizontal wall. The lower end of the duct 102 is free. This duct is in communication with the inside of the lower element 94, such that, when the upper element 92 and the lower element 94 of the air collection means 90 are interlocked, the duct 102 plays the role of an outlet duct for the air that was allowed into the air collection means 90 by means of the air inlet duct 98.

The upper end of the vertical circular wall 104 of the lower element 14 comprises, on its internal face, a shoulder 104$_1$. This shoulder is made over the entire circumference of the wall 104. It is also intended to facilitate the fitting together of the upper element 92 and the lower element 94, owing to the fact that the ends of the walls 100 and 104 have a cross section of complementary shape, facilitating the fitting together. It is important in the first place for this fitting together to be reversible. Once fitted together, the elements 92 and 94 should be able to disengage from one another.

An alternative means of fitting together the elements 92 and 94 may be fitting together by screwing one element onto the other. To this end, the end of the wall of one of the elements 92 or 94 may carry a male thread and the end of the wall of the second element a corresponding female thread.

The important thing is that the collection means is hermetically closed, in order to prevent any parasitic entry of air.

According to one particular mode of use of the air collection means, the lower end of the air outlet duct 102 may be connected to an air suction pump (not represented) or any equivalent pumping means.

A cartridge 110 is arranged inside the air collection means 90. To do this, the elements 92 and 94 constituting the air collection means 90 are separated. The cartridge 110 is placed to bear in the lower element 94 of the air collection means 90. The upper element 92 is then repositioned on the lower element 94 and these two means are interlocked. The assembly constituted of the air collection means 90 and the cartridge 110 is then either connected to a recycling circuit, or connected to a pumping device, in order to bring about circulation of the air inside the air collection means 10, as described above.

The cartridge 110 represented in longitudinal section has the general shape of a cylinder with a low height and a substantially circular transverse section. The upper end of the cylinder is free, whereas the lower end is constituted of a wall 112. This wall 112 serves as a support for the lysis means 118 and constitutes the microorganism retaining zone. These lysis means are constituted of beads, as described above. The beads are kept in place in the form of one or more superimposed layers by means of a gelled material as described above, deposited in the form of a layer, in which the layer(s) of beads is (are) embedded.

Figure 13:
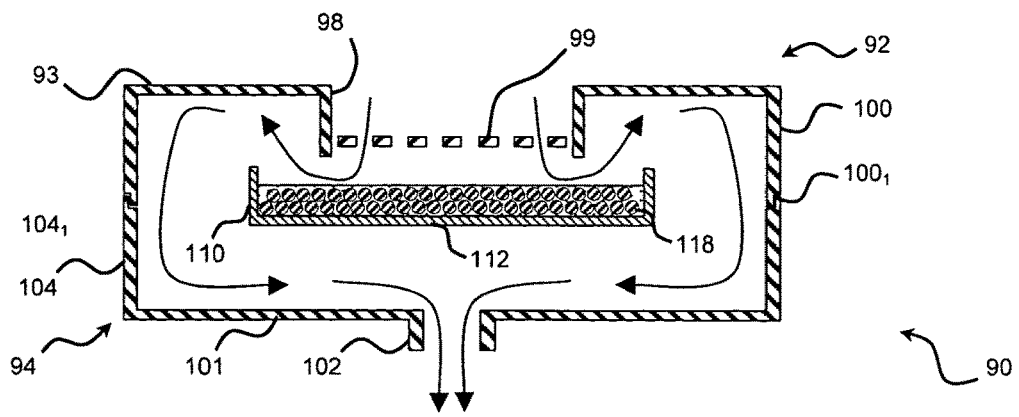
FIG. 13 represents a view in longitudinal section of the air collection means in which a cartridge has been placed, during the step of collecting the microorganisms, according to a second embodiment.

When the circulation of air in the air collection means is initiated, the path followed by said air is represented by the arrows in FIG. 13. Thus, it is noted that the air enters the air collection means 90 via the air inlet duct 98. By virtue of the screen 99, it is distributed homogeneously and breaks on the upper layer of beads 118, leading, at this site, to the retention, by impaction, of the microorganisms transported in the air flow, at the surface of the gelled material or of the culture medium.

The air, for its part, continues its route, drawn by the pumping means. It rises back up along the internal face of the wall of the cartridge 110. It redescends along the external face of this same wall and again becomes converted into a centralized flow at the entry of the air outlet duct 102, which escapes from the air collection means 90 via said air outlet duct.

Once the air collection has been carried out, the elements 92 and 94 of the air collection means 90 are unfastened and the cartridge 110 is recovered.

Figure 14:
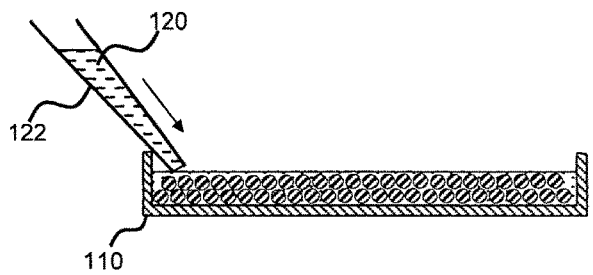
FIG. 14 represents a view in longitudinal section of the cartridge, during the step of manual distribution of the liquid of interest, according to the second embodiment.
Figure 15:
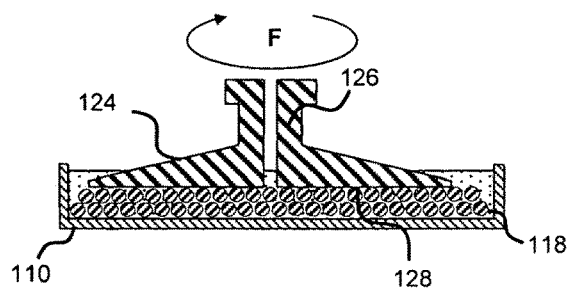
FIG. 15 represents a view in longitudinal section of the means for recovering nucleic acids, placed in the cartridge, during the step of mechanical lysis of the microorganisms, according to the second embodiment.

The step of distribution of the liquid of interest then takes place, as represented in FIG. 14. During this step, the manipulator deposits, in the cartridge 110, a given volume of liquid of interest 120 using a pipette 122, partially represented in FIG. 14. As explained above, the liquid of interest may, for example, be a lysis buffer. The contact between the liquid of interest and the gelled material trapping the beads leads to the suspending of said material and therefore the suspending of the beads themselves. The volume of liquid of interest deposited in the cartridge 110 may, for example, be 0.5 ml.

Once this step has been carried out, the manipulator places in the cartridge 110 a means 124 for recovering nucleic acids. Unlike the means 40 described in the first embodiment, the means 124 comprises neither a drawing up/delivering means nor a cavity capable of receiving the liquid of interest. This means 124 has a substantially cylindrical transverse section and has, in its upper part, a preferential gripping zone 126. The lower wall 128 of the means 124 is substantially flat and bears against the beads. The lysis is then carried out by rotation of the means 124 in the direction of the arrow F around its axis of symmetry, by the manipulator. The rotating of the wall 128 leads to the rotating of the beads 118 around the axis of symmetry. This double rotation leads to mechanical lysis of the microorganisms which are trapped between the beads 118 and the wall 128. This results in release of the nucleic acids into the liquid of interest.

Figure 16:
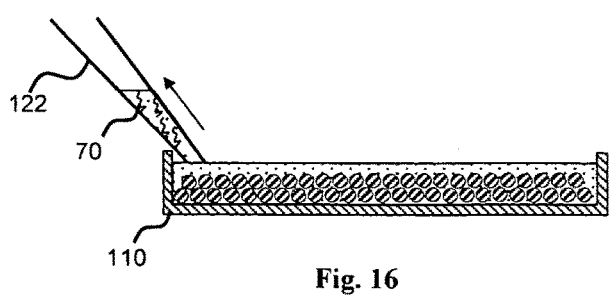
FIG. 16 represents a view in longitudinal section of the means for recovering nucleic acids, placed in the cartridge, during the step of drawing up the liquid of interest containing the nucleic acids, according to the second embodiment.

Once the lysis step has been completed and the nucleic acids released, the liquid of interest, loaded with said nucleic acids 70, is drawn up by the manipulator by means of the pipette 122, as represented in FIG. 16.

Once all the liquid of interest is in the pipette, said liquid can be transferred into an analyzing device in order to undergo therein the various nucleic acid treatment steps, as described above. It can also be placed in a container in order to be stored or in any device intended for carrying out steps prior to the nucleic acid treatment steps. Such a step may, for example, be a purification step, intended to concentrate the nucleic acids by separating them from the cellular constituents still present. Such a step is particularly relevant when the device according to the invention is used in its second embodiment, since, by virtue of the simple design of the latter, the liquid of interest loaded with nucleic acids does not undergo any filtering, as it does in the device according to the first embodiment and as explained above.

EXAMPLES

Example 1

Figure 17:
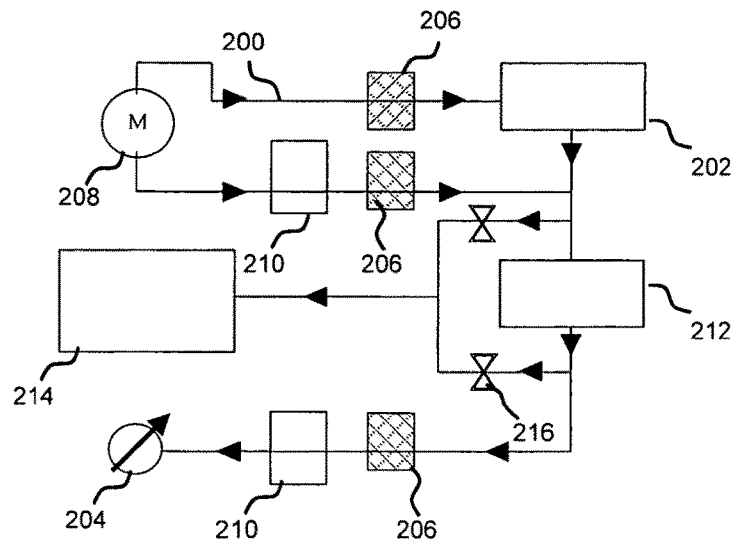
FIG. 17 represents a functional scheme of a test bench intended to test the capacity for capture of bacteria contained in aerosols, with the device according to the invention.

Measurement of the Efficiency of Capture of *Bacillus subtilis* Spores Contained in an Aerosol Using the Device According to the Invention A leaktight test bench was designed in order to carry out this measurement. This test bench is represented in FIG. 17. It is constituted of a closed air circuit 200, fed with aerosols by an aerosol generator 202. This generator makes it possible to introduce, into the air flow, a constant amount of *Bacillus subtilis* (CIP 52.62) spores, from a suspension of spores of known concentration. Suitable aerosol generators are, for example, sold by the company TSI. The air is circulated in the circuit by means of a suction pump 204. Three THE filters 206 are present all along the circuit so as to make it possible to remove the particles, in particular the particles of dust, contained in the air. A manometer 208 makes it possible to verify the pressure in the circuit and two flow meters 210 make it possible to verify the flow rate of the air in the circuit. The device according to the invention is referenced 212. It is constituted of the air collection means 10, inside which a cartridge 30 is placed. The collection means is connected to the air circuit as explained above. Finally two sampling sources, in the air circuit, are positioned just upstream and just downstream of the device 212. The air sampled at these levels, in the form of constant fractions, goes to a spectrometer 214 for carrying out an aerodynamic measurement of the particles, i.e. the *Bacillus subtilis* spores, contained in the fractions. This spectrometer is an Aerodynamic Particle Sizer® model 3321, sold by the company TSI. The transfer of air into this ancillary circuit that goes to the spectrometer is carried out by means of valves 216, which make it possible to permit or prevent the samplings, either upstream, or downstream of the device 212. The differential analysis of the upstream and downstream fractions makes it possible to calculate the efficiency of capture of the *Bacillus subtilis* spores by the device according to the invention.

The flow rate of air passing through the device according to the invention is 50 l/min under controlled humidity and temperature conditions (25° C., 35% relative humidity). This flow rate is obtained by means of the pump 204.

The capture efficiency of the device according to the invention was studied under the following two conditions:
  determination of the efficiency of capture of *Bacillus subtilis* spores, with a cartridge in which the beads 36 are positioned in the cartridge without gelled material,
  determination of the efficiency of capture of *Bacillus subtilis* spores, with a cartridge in which the beads 36 are positioned in the cartridge and covered with a fine film-coating of glycerol. This product is sufficiently viscous to provide good adhesion of the aerosols to the collection plate and does not generally interfere with the subsequent molecular analysis.

Figure 18:
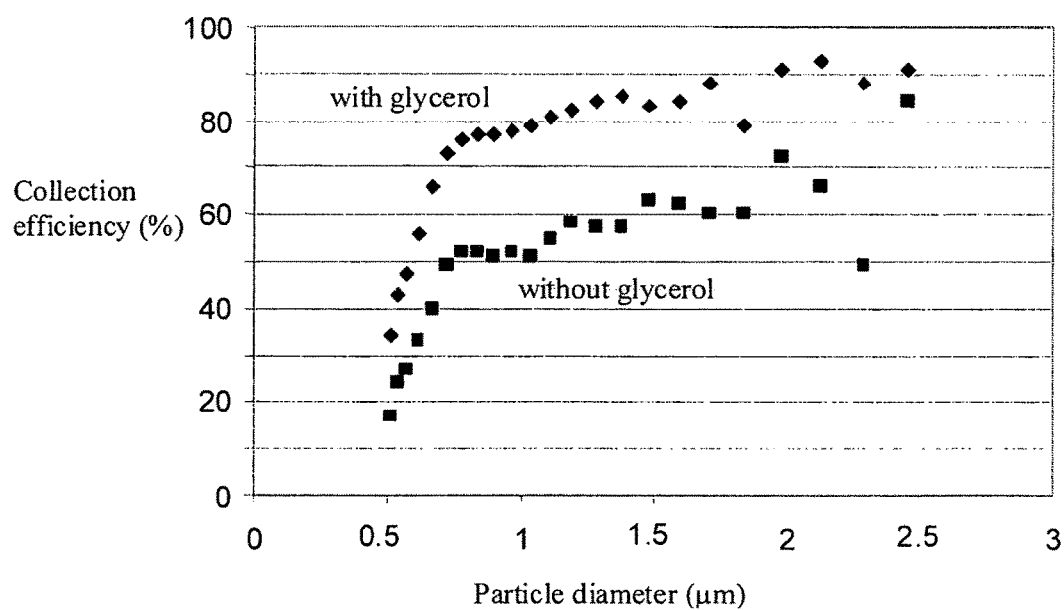
FIG. 18 is a graph showing the collection efficiency of the device according to the invention as a function of the size of the aerosol particles produced.
Figure 19:
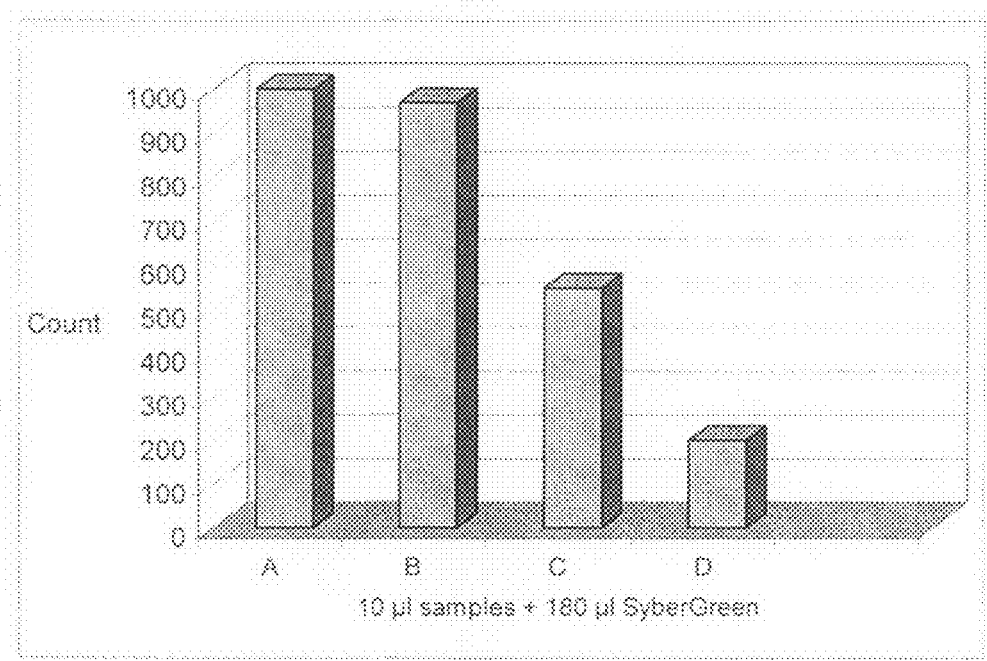
FIG. 19 is a graph comparing the bacterial lysis efficiency with the device according to the invention and alternative methods of the prior art.

The results obtained with and without glycerol are shown in FIG. 18. In this figure, it is possible to correlate the efficiency of collection of the *Bacillus subtilis* spores as a function of the diameter of the particles of aerosols produced by the generator 202.

It appears that, in the absence of gelled material covering the beads 36 in the cartridge, the efficiency of spore collection by the device according to the invention can range up to more than 70%.

In the presence of gelled material covering the beads 36 in the cartridge, the collection efficiency climbs to more than 90%.

The increase in the collection efficiency in the presence of a gelled material, of the glycerol type, is explained by the fact that the spores remain stuck to this material. In the absence of gelled material, a slight phenomenon of spore rebound on the beads occurs, preventing them from remaining stuck to the beads.

Example 2

Determination of Lysis Efficiency by Comparison Between the Lysis Method According to the Invention and Alternative Methods In this case, 3 methods are compared with the lysis method according to the invention:

- method of mechanical lysis using the FastPrep™ instrument (type FP 120, BIO101, sold by the company Thermo Electron Corporation);
- method of enzyme lysis, using lysozyme;
- method using a chaotropic agent (guanidium isothiocyanate, GuSCN) combined with a step of heating the cell suspension to 90° C., followed by three steps of freezing-thawing the cells.

In this example, the cells used are *Bacillus cereus* in suspension.

After the lysis step, the recovered nucleic acids are purified using the NucliSENS® easyMAG™ extraction system sold by the applicant. The purified nucleic acids are finally quantified using the SYBRGreen detection method (Molecular Probes). The precise steps of the comparative study are described below:

Step 1: Preparation of the *Bacillus cereus* Suspension

A culture of *Bacillus cereus* is carried out on agar culture medium in TSA (trypticase soja) plates. Bacterial colonies are recovered on the agar and washed in a NucliSENS® easyMAG™ extraction buffer 3 (ref. 280132), sold by the applicant. Once the cells have been washed, they are diluted in 5 ml of the same extraction buffer, in order to obtain a bacterial suspension having an optical density of 0.5 at a wavelength of 600 nm.

Step 2a: Lysis with the Fastprep® Instrument 0.5 ml of the bacterial suspension is transferred to a 2 ml tube filled with a mixture of 1 g of glass beads (equal fractions of beads of various sizes: 150-212 μm, 420-600 μm and 700-1180 μm). The FastPrep® instrument is used at its maximum speed (setting at 6.0), for 60 sec. Once the lysis has been completed, 100 μl of lysate are transferred into the NucliSENS® easyMAG™ instrument so as to undergo a purification step.

Step 2b: Lysis with the Device According to the Invention 0.3 ml of bacterial suspension is transferred into a cartridge equivalent to the cartridge 110 described above. The cartridge is then filled with 0.4 g of mixtures of glass beads (equal fractions of beads of various sizes: 150-212 μm, 212-300 μm and 420-600 μm). The cartridge is brought into contact with a means for recovering nucleic acids. The latter is rotated for 2 min at 2000 rpm. Once this lysis step has been carried out, 100 μl of lysate are transferred into the NucliSENS® easyMAG™ instrument so as to undergo a purification step.

Step 2c: Enzyme Lysis

In this method of lysis with lysozyme, 100 μl of bacterial suspension are mixed with 100 μl of a solution of lysozyme (50 mg/ml). The mixture is incubated for 30 min at 37° C. After this incubation, the entire lysate (200 μl) is transferred into the NucliSENS® easyMAG™ instrument so as to undergo a purification step.

Step 2d: Chaotropic Lysis

100 μl of bacterial suspension are mixed with 100 μl of a concentrated solution of GuSCN (5 mol/l) and the whole mixture is incubated for 30 min. After this incubation, the entire lysate (200 μl) is transferred into the NucliSENS® easyMAG™ instrument so as to undergo a purification step.

Step 3: Purification of the Lysate Using the NucliSENS® easyMAG™ Instrument

The purification step is carried out using the generic extraction protocol of the NucliSENS® easyMAG™ instrument. 2 ml of NucliSENS® easyMAG™ lysis buffer (ref. 280134) sold by the applicant and 50 μl of a suspension of NucliSENS® easyMAG™ magnetic silica particles (ref. 280133) sold by the applicant are added to each lysate. The nucleic acids of each of the lysates are eluted in 25 μl of NucliSENS® easyMAG™ extraction buffer 3.

Step 4: Nucleic Acid Detection

In order to determine the amount of nucleic acids in each of the eluates, 10 μl of said eluates are placed in a 0.2 ml PCR tube. 180 μl of SyberGreen solution are then added to the samples and the fluorescence signal is measured using the NucliSENS EasyQ® instrument sold by the applicant.

The results of the fluorescence measurements are given in FIG. 19. The correspondence is the following:

A=lysis with the FastPrep® instrument
B=lysis with the device according to the invention
C=enzyme lysis
D=chaotropic lysis By analyzing FIG. 19, it is noted that the lysis efficiency of the device according to the invention is similar to that of the FastPrep® mechanical lysis method. These two mechanical methods are, moreover, significantly more efficient than the method of enzyme lysis or of chemical lysis using the chaotropic agent.

Example 3

Lysis of a *Bacillus* Suspension Using the Device According to the Invention in Combination with Detection by the NASBA Method 0.3 ml of a suspension of *Bacillus cereus* diluted in the NucliSENS® easyMAG™ extraction buffer 3 is introduced into the cartridge according to the invention. The lysis method according to the invention, as described in the preceding example, is reproduced for 2 min. After the lysis step, 5 μl of lysate are used to carry out a detection by the real time NASBA method using primers and probes specific for *Bacillus cereus*, by fluorescence using the NucliSENS EasyQ® instrument. The target gene used for the detection is the EF-tu gene. The size of the amplification product is 115 nucleotides.

Various amounts of *Bacillus* ranging from 6 to $6\times10^5$ were used.

FIG. 20 shows the real time production of fluorescence as a function of the various amounts of *Bacillus cereus* introduced into the device according to the invention. In this figure, the correspondence is the following:

a=sample with $6\times10^5$ *Bacilli*
b=sample with $6\times10^4$ *Bacilli* c=sample with 6×10³ *Bacilli*
d=sample with 600 *Bacilli*
e=sample with 60 *Bacilli*
f=sample with 6 *Bacilli*
g=sample without *Bacillus*.

Figure 20:
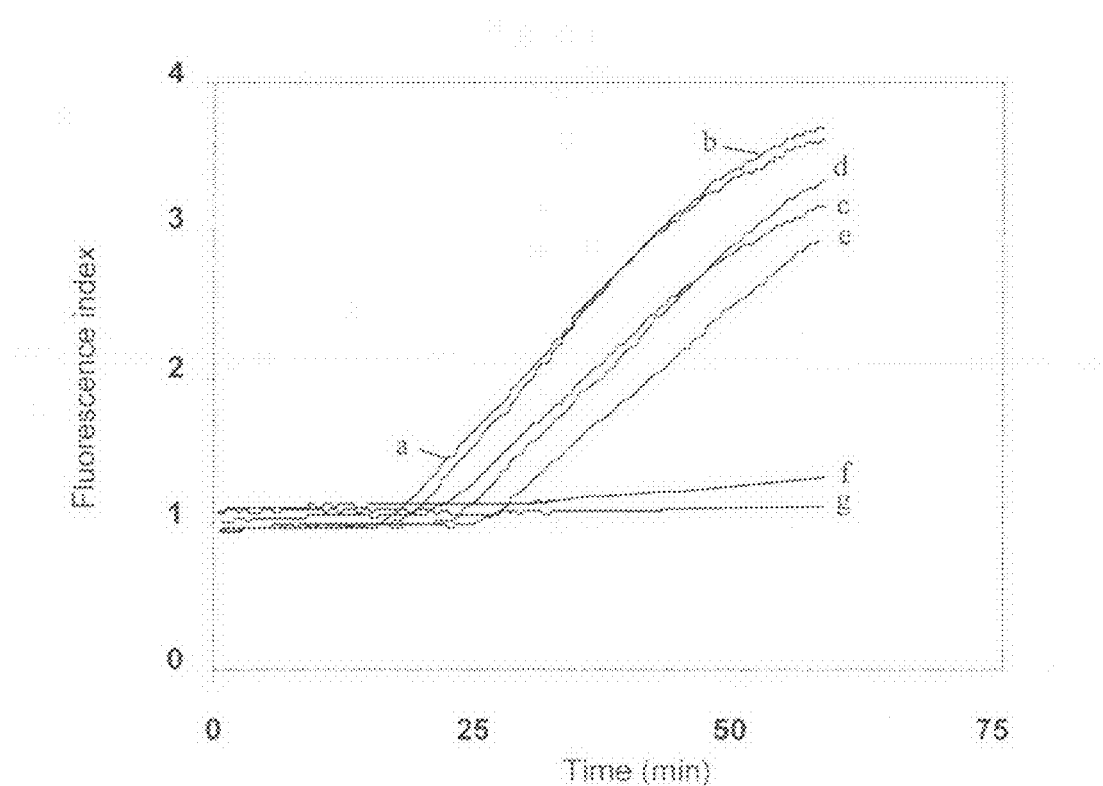
FIG. 20 is a graph showing the real time detection, using the Real Time NASBA technology, of the bacteria contained in various suspensions, after lysis of these bacteria and recovery of the nucleic acids by means of the device according to the invention.

From the viewpoint of FIG. 20, a very good correlation between the level of fluorescence detected and the number of bacteria contained in the sample is observed. Furthermore, a significant difference is noted between a sample containing no bacteria and a sample containing only 6 thereof. Finally, it can be deduced from the results of this analysis that the device according to the invention offers a level of performance appropriate for the use of a nucleic acid amplification method of the NASBA type.

It should be noted that the sensitivity of this analysis could be improved by concentrating the nucleic acids, before carrying out the amplification by the NASBA method. Such a concentration step can be carried out using, for example, the NucliSENS® easyMAG™ instrument.

Example 4

Analysis of a Whole Blood Sample Using the Device According to the Invention

In this example, the device according to the invention is used to analyze a whole blood sample to which a population of *Bacillus cereus* has been added. The blood sample is derived from a healthy individual.

A culture of *Bacillus cereus* is carried out on agar culture medium in TSA (trypticase soja) plates. Bacterial colonies are recovered on the agar and washed with a NucliSENS® easyMAG™ extraction buffer 3. Once the cells have been washed, they are diluted in 5 ml of the same extraction buffer, in order to obtain a bacterial suspension having an optical density of 0.5 at a wavelength of 600 nm. This stock suspension contains approximately $2.2 \times 10^7$ bacteria/ml. This stock suspension is diluted in NucliSENS® easyMAG™ extraction buffer 3, in order to obtain a suspension having different concentrations, one at $10^3$ bacteria/ml and one at $10^5$ bacteria/ml.

The protocol subsequently used is the following for each of the dilution suspensions:
1. 24 µl of dilution suspension are added to 150 µl of blood and mixed;
2. 125 µl of a NucliSENS® easyMAG™ extraction buffer 1 (ref. 280130) are introduced into a cartridge according to the invention;
3. the blood sample loaded with bacteria is, in turn, introduced into the cartridge;
4. the lysis step is carried out by bringing the cartridge into contact with a means for recovering nucleic acids. The latter is rotated for 2 min at 2000 rpm;
5. 100 µl of lysate are drawn up into the cartridge;
6. purification of this lysate is carried out using the NucliSENS® easyMAG™ instrument as described in step 3 of example 2, enabling 25 µl of eluate to be recovered;
7. 5 µl of this eluate are used to carry out the amplification and the detection, using the Real Time NASBA technology.

Figure 21:
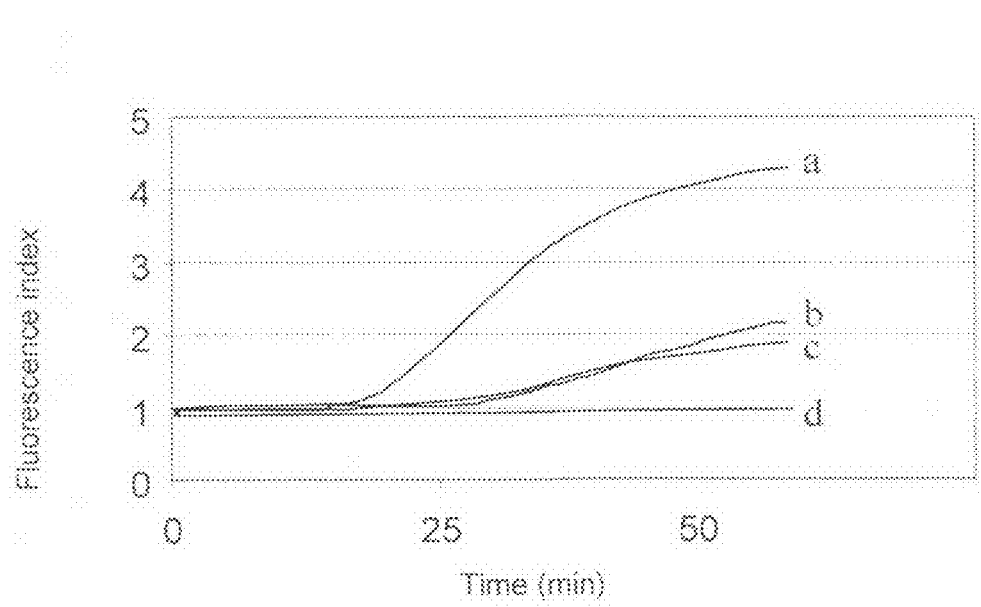
FIG. 21 is a graph showing the real time detection, using the Real Time NASBA technology, of the bacteria contained in various whole blood samples, after lysis of these bacteria and recovery of the nucleic acids by means of the device according to the invention.

The results are given in FIG. 21. In this figure, the correspondence is the following:
a=whole blood sample containing 53 *Bacilli* (dilution suspension at $10^5$ bacteria/ml)
b=whole blood sample containing 5 *Bacilli* (dilution suspension at $10^3$ bacteria/ml)
c=whole blood sample containing 5 *Bacilli* (dilution suspension at $10^3$ bacteria/ml)
d=whole blood sample without bacteria.

The results given correspond to the dilution suspensions at $10^3$ and $10^5$ bacteria/ml. Moreover, the analysis for the suspension at $10^5$ bacteria/ml was duplicated.

From the viewpoint of the volume of dilution suspensions introduced into the cartridge according to the invention, the actual amounts of bacteria are 5 and 530 bacteria, respectively, for the suspensions at $10^3$ and $10^5$ bacteria/ml.

It is thus noted that the analysis of a sample containing only 5 bacteria with the device according to the invention produces a positive detection signal (curves b and c), which can be clearly distinguished from the result obtained with the sample containing no bacteria (curve d).

It is noted, moreover, that even with small amounts of bacteria, the results are reproducible; this is shown by curves b and c.

It should be noted that this very good sensitivity was merely obtained using only 5 µl of the 25 µl obtained at the end of the purification step. This sensitivity can therefore be further improved by carrying out a step of concentrating the sample, after purification.

It thus emerges from these examples that the device according to the invention is an effective tool for collecting the bacteria contained in a sample of air, lyzing them, and allowing the recovery of the nucleic acids from said bacteria for analysis. For this, the device used will be constituted, firstly, of a cartridge introduced into the air collection means and, secondly, of the cartridge containing the collected bacteria, combined with the means for recovering nucleic acids.

The device according to the invention is also entirely suitable for the analysis of clinical samples, such as whole blood samples. In this case, the cartridge is used without an air collection means. The liquid sample is placed in the cartridge and then the latter is combined with the means for recovering nucleic acids in order to lyze the bacteria and to recover the nucleic acids.

The invention claimed is:

1. A cartridge which can be positioned inside an air collection device and receive a means for recovering nucleic acids, said cartridge being substantially cylindrical and having an upper end and lower end, said cartridge comprising a microorganism retaining zone, said retaining zone comprising microorganism lysis means for lysing the microorganisms, wherein
    the upper end of the cartridge is open,
    the lower end is constituted of a wall, having, in its center, an orifice, there being, along an extension of said orifice, a duct extending, inside said cartridge, and
    the microorganism retaining zone comprises a material configured to retain the microorganisms, configured to keep the lysis means in place, and configured to dissolve in the presence of a liquid to release the lysis means from the material.

2. The cartridge as claimed in claim 1, in which the material is a gelled material.

3. The cartridge as claimed in claim 2, in which the gelled material is a microorganism culture medium.

4. The cartridge as claimed in claim 1, also comprising a means for connection of an analyzing device.

5. The cartridge as claimed in claim 4, in which the lysis means comprises beads as the lysis means.

6. The cartridge as claimed in claim 5, in which the diameter of the beads is between 200 and 600 µm.

7. A device for collecting microorganisms contained in the air, said device comprising:
- an air collection device, comprising an upper element comprising an air inlet duct and a lower element comprising an air outlet duct, it being possible for said upper and lower elements to be interlocked with one another such that a current of air can be created inside said air collection device;
- the cartridge as claimed in claim 1 being positioned inside said air collection device.

8. The device as claimed in claim 7, in which the air collection device is capable of being connected to an air recycling circuit.

9. A device for microorganism lysis, said device comprising:
- the cartridge as claimed in claim 1, said cartridge comprising microorganisms placed in the microorganism retaining zone;
- a substantially cylindrical means for recovering nucleic acids, that can be placed in the cartridge, said recovering means cooperating with the microorganism lysis means in order to lyze said microorganisms and enable release of the nucleic acids.

10. The device as claimed in claim 9, in which the means for recovering nucleic acids comprises a means for drawing up/delivering liquid.

11. The device as claimed in claim 9, in which the means for recovering nucleic acids also comprise a liquid storage zone.

12. The device as claimed in claim 9, in which the internal diameter of the cartridge is greater than the external diameter of the means for recovering nucleic acids, such that, when the means for recovering nucleic acids is fitted into the cartridge, the distance separating the internal wall of the cartridge from the external wall of the means for recovering nucleic acids is sufficiently large to allow the lysis means to sit in this interstitial space and sufficiently small for the lysis means to be in contact with one or other of said walls.

13. A method for concentrating microorganisms contained in the air, said method comprising:
- a) placing the cartridge as claimed in claim 1 inside an air collection device, such that the retaining zone, inside said cartridge, is in communication with the air inlet duct of the air collection device,
- b) causing air to enter said air collection device, and
- c) concentrating the microorganisms contained in the air in the retaining zone of the cartridge.

14. The method of concentration as claimed in claim 13, which also comprises a step d) comprising growing the microorganisms in the retaining zone.

15. The method of concentration as claimed in claim 13, in which the microorganisms are retained on the lysis means present in the retaining zone.

16. A method for the lysis of microorganisms contained in the air, said method comprising:
- a) placing the cartridge as claimed in claim 1 inside an air collection device, such that the retaining zone, inside said cartridge, is in communication with the air inlet duct of the air collection device,
- b) causing air to enter said air collection device,
- c) concentrating the microorganisms contained in the air, in the retaining zone of the cartridge,
- d) removing the cartridge from the air collection device,
- e) placing the means for recovering nucleic acids in the cartridge,
- f) introducing a liquid into the cartridge, which leads to the lysis means located in the microorganism retaining zone of the cartridge being placed in suspension, and
- g) mechanically lyzing the microorganisms by rotating the means for recovering nucleic acids, inside the cartridge, said means for recovering nucleic acids rotating the lysis means on which the microorganisms are retained.

17. A method for the lysis of microorganisms contained in the air, said method comprising:
- a) placing the cartridge as claimed in claim 1 inside an air collection device, such that the retaining zone, inside said cartridge, is in communication with the air inlet duct of the air collection device,
- b) causing air to enter said air collection device by,
- c) concentrating the microorganisms contained in the air, in the retaining zone of the cartridge,
- d) removing the cartridge from the air collection device,
- e) fitting the means for recovering nucleic acids into the cartridge,
- f) causing the delivery of a liquid previously placed in a storage zone of the device for recovering nucleic acids, said delivery being obtained by a drawing up/delivering means for recovering nucleic acids, the liquid thus delivered filling an interstitial space located between the means for recovering nucleic acids and the cartridge, which leads to the lysis means located in the microorganism retaining zone of the cartridge being placed in suspension, said lysis means coming to sit between a vertical internal wall of the cartridge and a vertical external wall of the means for recovering nucleic acids, and
- g) mechanically lysing the microorganisms by rotating the means for recovering nucleic acids, inside the cartridge, said means for recovering nucleic acids rotating the lysis means on which the microorganisms are retained.

18. A method for the extraction of nucleic acids from microorganisms contained in the air, said method comprising:
- a) placing the cartridge as claimed in claim 1 inside an air collection device, such that the retaining zone, inside said cartridge, is in communication with the air inlet duct of the air collection device,
- b) causing air to enter said air collection device,
- c) concentrating the microorganisms contained in the air, in the retaining zone of the cartridge,
- d) removing the cartridge from the air collection device,
- e) placing the means for recovering nucleic acids in the cartridge,
- f) introducing a liquid into the cartridge, which leads to the lysis means located in the microorganism retaining zone of the cartridge being placed in suspension, and
- g) mechanically lysing the microorganisms by rotating the means for recovering nucleic acids, inside the cartridge, said means for recovering nucleic acids rotating the lysis means on which the microorganisms are retained, and
- h) drawing up the liquid containing the nucleic acids of said microorganisms, released during the lysis.

19. A method for the extraction of nucleic acids from microorganisms contained in the air, said method comprising:
- a) placing the cartridge as claimed in claim 1 inside an air collection device, such that the retaining zone, inside said cartridge, is in communication with the air inlet duct of the air collection device,
- b) causing air to enter said air collection device, c) concentrating the microorganisms contained in the air, in the retaining zone of the cartridge,
d) removing the cartridge from the air collection device,
e) fitting the means for recovering nucleic acids into the cartridge,
f) causing the delivery of a liquid previously placed in a storage zone of the device for recovering nucleic acids, said delivery being obtained by a drawing up/delivering means for recovering nucleic, acids, the liquid thus delivered filling an interstitial space located between the means for recovering nucleic acids and the cartridge, which leads to the lysis means located in the microorganism retaining zone of the cartridge being placed in suspension, said lysis means coming to sit between a vertical internal wall of the cartridge and a vertical external wall of the means for recovering nucleic acids,
g) mechanically lysing the microorganisms by rotating the means for recovering nucleic acids, inside the cartridge, said means for recovering nucleic acids rotating the lysis means on which the microorganisms are retained, thus releasing the nucleic acids from said microorganisms, and
h) causing the liquid in the storage zone to be drawn up, said drawing up being obtained by the drawing up/delivering means for recovering nucleic acids, the liquid of interest thus drawn up containing the nucleic acids of said microorganisms, released during the lysis.

20. The method as claimed in claim 16, comprising an additional step d') comprising growing the concentrated microorganisms in the retaining zone of the cartridge.

21. The method as claimed in claim 20, in which the growing is obtained by incubation of the cartridge in an incubator for a period of time ranging from 2 to 24 hours.

22. A method for the lysis of microorganisms, said method comprising:
a) obtaining the cartridge, as claimed in claim 1, in which microorganisms are concentrated in the retaining zone,
b) fitting the means for recovering nucleic acids into the cartridge,
c) causing the delivery of a liquid previously placed in a storage zone of the means for recovering nucleic acids, said delivery being obtained by a drawing up/delivering means for recovering nucleic acids, the liquid thus delivered filling an interstitial space located between the means for recovering nucleic acids and the cartridge, which leads to the lysis means located in the microorganism retaining zone of the cartridge being placed in suspension, said lysis means coming to sit between a vertical internal wall of the cartridge and a vertical external wall of the means for recovering nucleic acids, and
d) mechanically lysing the microorganisms by rotating the means for recovering nucleic acids, inside the cartridge, said means for recovering nucleic acids rotating the lysis means on which the microorganisms are retained.

23. A method for the lysis of microorganisms, said method comprising:
a) obtaining the cartridge, as claimed in claim 1, in which microorganisms are concentrated in the retaining zone,
b) placing the means for recovering nucleic acids in the cartridge,
c) introducing a liquid into the cartridge, which leads to the lysis means located in the microorganism retaining zone of the cartridge being placed in suspension, and
d) mechanically lysing the microorganisms by rotating the means for recovering nucleic acids, inside the cartridge, said means for recovering nucleic acids rotating the lysis means on which the microorganisms are retained.

24. A method for the extraction of nucleic acids from microorganisms, said method comprising:
a) obtaining the cartridge, as claimed in claim 1, in which microorganisms are concentrated in the retaining zone,
b) fitting the means for recovering nucleic acids into the cartridge,
c) causing the delivery of a liquid previously placed in a storage zone of the means for recovering nucleic acids, said delivery being obtained by the drawing up/delivering means for recovering nucleic acids, the liquid thus delivered filling an interstitial space located between, the means for recovering, nucleic acids and the cartridge, which leads to the lysis means located in the microorganism retaining zone of the cartridge being placed in suspension, said lysis means coming to sit between a vertical internal wall of the cartridge and a vertical external wall of the means for recovering nucleic acids,
d) mechanically lysing the microorganisms by rotating the means for recovering nucleic acids, inside the cartridge, said means for recovering, nucleic acids rotating the lysis means on which the microorganisms are retained, thus releasing the nucleic acids from said microorganisms, and
e) causing the liquid in the storage zone of the means for recovering nucleic acids to be drawn up, said drawing up being obtained by the drawing up/delivering means recovering nucleic acids, the liquid of interest thus drawn up containing the nucleic acids of said microorganisms, released during the lysis.

25. A method for the extraction of nucleic acids from microorganisms, said method comprising:
obtaining the cartridge, as claimed in claim 1, in which microorganisms are concentrated in the retaining zone,
b) placing the means for recovering nucleic acids in the cartridge,
c) introducing a liquid into the cartridge, which leads to the lysis means located in t e microorganism retaining zone of the cartridge being placed in suspension, and
d) mechanically lysing the microorganisms by rotating the means for recovering nucleic acids, inside the cartridge, said means for recovering nucleic acids rotating the lysis means on which the microorganisms are retained, and
e) drawing up the liquid containing the nucleic acids of said microorganisms, released during the lysis.

26. A method for the lysis of microorganisms, said method comprising:
a) introducing a liquid sample containing said microorganisms into the cartridge as claimed in claim 1, in a vicinity of the retaining zone, such that said liquid sample leads to the lysis means located in said microorganism retaining zone of the cartridge being placed in suspension,
b) placing the means for recovering nucleic acids in the cartridge,
c) mechanically lysing the microorganisms by rotating the means for recovering nucleic acids, inside the cartridge, said means for recovering nucleic acids rotating the lysis means on which the microorganisms are retained.

27. A method for the extraction of nucleic acids from microorganisms, said method comprising:
a) introducing a liquid sample containing said microorganisms into the cartridge as claimed in claim 1 in a vicinity of the retaining zone, such that said liquid sample leads to the lysis means located in said microorganism retaining zone of the cartridge being placed in suspension,
b) placing the means for recovering nucleic acids in the cartridge,
c) mechanically lysing the microorganisms by rotating the means for recovering nucleic acids, inside the cartridge, said means for recovering nucleic acids rotating the lysis means on which the microorganisms are retained,
d) drawing up the liquid containing the nucleic acids of said microorganisms, released during the lysis.

28. A method for identifying one or more microorganisms contained in a sample, the method comprising:
isolating the nucleic acids from the microorganisms contained in said sample by means of the device as claimed in claim 7,
identifying the microorganism(s) thus isolated.

29. The method of identification as claimed in claim 28, also comprising an intermediate step consisting in purifying the nucleic acids.

30. The method of identification as claimed in claim 28, in which the identification step further comprises:
specifically amplifying the isolated nucleic acids, and detecting the nucleic acids thus amplified.

31. The method of identification as claimed in claim 28, in which the identification step is carried out in an identification device in fluid communication with the cartridge, the cartridge comprising microorganisms placed in the microorganism retaining zone.

32. The method of identification as claimed in claim 31, in which the isolated nucleic acids are transferred from a substantially cylindrical means for recovering nucleic acids, that can be placed in the cartridge, to the identification device.

33. The method of identification as claimed in claim 32, in which the transfer of the nucleic acids is obtained by delivery of a liquid containing the nucleic acids, said liquid being contained in a storage zone of the device for recovering nucleic acid, by a drawing up/delivering means for recovering nucleic acids.

34. The cartridge as claimed in claim 1, in which the material is agarose.

* * * * *